United States Patent
Mori et al.

(10) Patent No.: US 9,683,997 B2
(45) Date of Patent: Jun. 20, 2017

(54) MONOCLONAL ANTIBODY RECOGNIZING HUMAN PAPILLOMAVIRUS (HPV) L2 PROTEIN AND METHOD FOR MEASURING HPV-NEUTRALIZING ANTIBODY TITER USING THE SAME

(71) Applicant: Japan Health Sciences Foundation, Tokyo (JP)

(72) Inventors: Seiichiro Mori, Tokyo (JP); Tadahito Kanda, Tokyo (JP)

(73) Assignee: Japan Health Sciences Foundation, Tokyo (JP)

(*) Notice: Subject to any disclaimer, the term of this patent is extended or adjusted under 35 U.S.C. 154(b) by 0 days.

(21) Appl. No.: 14/973,240

(22) Filed: Dec. 17, 2015

(65) Prior Publication Data

US 2016/0154007 A1 Jun. 2, 2016

Related U.S. Application Data

(62) Division of application No. 13/997,902, filed as application No. PCT/JP2011/079994 on Dec. 26, 2011, now Pat. No. 9,279,161.

(30) Foreign Application Priority Data

Dec. 27, 2010 (JP) ................................. 2010-291067

(51) Int. Cl.
*C12Q 1/70* (2006.01)
*G01N 33/68* (2006.01)
*C07K 16/08* (2006.01)
*G01N 33/574* (2006.01)
*A61K 47/48* (2006.01)
*G01N 33/569* (2006.01)
*A61K 39/00* (2006.01)

(52) U.S. Cl.
CPC ... *G01N 33/6854* (2013.01); *A61K 47/48776* (2013.01); *C07K 16/084* (2013.01); *C12Q 1/70* (2013.01); *G01N 33/56983* (2013.01); *G01N 33/57411* (2013.01); *A61K 2039/505* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2333/025* (2013.01); *G01N 2800/26* (2013.01); *G01N 2800/52* (2013.01)

(58) Field of Classification Search
None
See application file for complete search history.

(56) References Cited

FOREIGN PATENT DOCUMENTS

| EP | 2168977 A1 | 3/2010 |
| WO | WO-2007/018049 A1 | 2/2007 |
| WO | WO-2009/001867 A1 | 12/2008 |
| WO | WO-2010/070052 A2 | 6/2010 |

OTHER PUBLICATIONS

International Search Report (ISR) in PCT/JP2011/079994 issued Feb. 2, 2012.
Written Opinion of the International Searching Authority in PCT/JP2011/079994 issued Feb. 2, 2012.
International Preliminary Report on Patentability (IPRP) in PCT/JP2011/079994 issued Jul. 2, 2013.
Alphs, H. H. et al., *PNAS*, 2008, 5850-5855.
Gambhira, R. et al., *Journal of Virology*, 2007, vol. 81, 13927-13931.
Kanda, T. et al., *Clinical Virology*, 2009, vol. 37, 145-152.
Kanda, T. et al., *Human Vaccines*, 2009, vol. 5, 43-45.
Kanda, T., et al., *The Journal of Pediatric Practice*, 2008, vol. 8, 1319-1323.
Kawana, K, et al., *Vaccine*, 2003, 21: 4256-4260.
Kawana, K. et al., *Journal of Virology*, 1999, vol. 73, 6188-6190.
Kawana, K. et al., *Virology*, 1998, vol. 245, 353-359.
Kondo, K. et al., *Journal of Medical Virology*, 2008, vol. 80, 841-846.
Kondo, K. et al., *Virology*, 2007, vol. 358, 266-272.
Xu, Y. et al., *Journal of Medical Microbiology*, 2007, vol. 56, 907-913.
Zhou, J. et al., *Virology*, 1991, 185: 251-257.
zur Hausen H. *Biochim Biophys Acta*, 1996, 1288: F55-78.
NZ Office Action for New Zealand Application No. 611168, issued on Dec. 9, 2013.
European Search Report for Application 11853408.0 issued Mar. 20, 2014.
CN Office Action in corresponding Chinese patent Application No. 20118063220.3 issued on Nov. 4, 2014.
SG Office Action, issued Jun. 16, 2015, in corresponding SG Patent Application No. 201304527-3 (6 pages).
Russian Office Action issued Jul. 13, 2015, in Russian Application No. 2013-129203. (5 Pages).
Japanese Office Action issued Nov. 10, 2015, in Japanese Application No. 2012- 550917. (4 Pages).

(Continued)

*Primary Examiner* — Nick Zou
(74) *Attorney, Agent, or Firm* — Mintz Levin Cohn Ferris Glovsky and Popeo, P.C.; David G. Conlin

(57) ABSTRACT

The present invention relates to the development of a monoclonal antibody which has binding activity to many high-risk types of HPV, etc. The present invention also provides a simple and high-throughput method for measuring cross-neutralizing antibody titers, which is used for assay of cross-neutralizing antibody against HPV in serum samples from subjects, etc. The method of the present invention for measuring cross-neutralizing antibody titers comprises the steps of: preparing a monoclonal antibody against a peptide having a specific amino acid sequence common to high-risk types of HPV; and assaying cross-neutralizing antibody using this monoclonal antibody.

7 Claims, 11 Drawing Sheets

(56) References Cited

OTHER PUBLICATIONS

Wikstrom et al. Levels of Immunoglobulin G Antibodies against Defined Epitopes of the L1 and L2 Capsid Proteins of Human Papillomavirus Type 6 are Elevated in Men with a History of Condylomata Acuminata. Journal of Clinical Microbiology, Jul. 1992, vol. 30, No. 7. p. 1795-1800.
Brown et al. Neutralization of human papillomavirus type 11 (HPV-11) by serum from women vaccinated with yeast-derived HPV-11 L1 virus-like particles: correlation with competitive radioimmunoassay titer. J Infect Dis. Nov. 1, 2001;184(9):11.
Taiwanese Office Action for Application No. 100148559, dated Jun. 22, 2015.
Thai Office Action issued Apr. 18, 2014 in corresponding Thai Patent Application No. 1301003584.
JP Office Action, issued Jun. 7, 2016, in corresponding JP Patent Application No. 2012-550917 (3 pages).
EP Office Action, issued Jun. 30, 2016, in corresponding EP Patent Application No. 11853408.0 (4 pages).
JP Notice of Allowance, issued Nov. 15, 2016, in corresponding JP Patent Application No. 2012-550917 (3 pages).

Figure 2

| L2 epitopes recognized by monoclonal antibodies 13B and 24B |

```
              56                 75
      13B    GGLGIGTGS TGGRTGY IPL           Double underline: epitope core
      24B    GGL GIGTGSGT TGYIPL
```

```
                        24B           13B
HPV16    50-SMGVFF GGLGIGTGSG TGGRTGY IPL-75
HPV18    49-*L*I*L ********** ******* ***-74
HPV31    50-******* *****S**** ******* V**-75
HPV58    49-*L***** ********** ******* V**-74
HPV33    49-*L***** ********** S****** V*I-74
HPV35    50-A *S S** V-75
HPV39    49-*L*I*L ****T***** ******* ***-74
HPV45    49-*L*I*L ********** S****** V**-74
HPV51    49-GL*I*L ********** S****** ***-74
HPV52    49-*L***** *****A*S** *A***** V**-74
HPV56    49-*LFTY** ****T*S*** *A***** V**-74
HPV59    49-*L*I*L ********** ******* ***-74
HPV66    49-*LFTY** *********S *A***** V**-74
HPV68    49-*L*I*L ********** ******* ***-74
HPV73    51-*I***** *****S***S ******* V**-76
HPV6     49-*L***** ********** ******* V**-74
HPV11    50-*L***** *****A*S** *A***** ***-75
```

Figure 7

Heavy-chain variable region
```
                                            CDR1                              CDR2
13B VH    EVQLQESGPGLVKPSQSLSLSCTVTGYSITSDSAWNWIRQFPGNKLEWMGYIT-FSGSTN
24B VH    EVQLQQSGTVLARPGASVKMSCKASVYSFFSN-WMHWVKQRPGQGLEWIGAIYPSTGATR
                                                      CDR3
13B VH    YNPSLKSRLSITRDTSKNQFFLQLRSVTTEDTATYYCTGFFLDYWGQGTTLTVSS
24B VH    YNQKFKDKAKLTAVTSADTAYMELSSLTDEDSAVYYCTG-YSLYWGQGTILTVSS
```

Light-chain variable region
```
                                       CDR1                              CDR2
13B VL    DVVMTQTPLSLPVSLGDQATISCRSSLSLVLSNRIPYLQWYLQKPGQSPKLLIYKVSNRF
24B VL    DVVMTQTPLTLSVTLGQPASISCKSSQSLLDSDGKTYLNWLLQRPGQSPKRLIYLVSKLD
                                                    CDR3
13B VL    SGVPDRFSGSGSGTDFTLKISRVEAEDLGVYFCSQSSHFPWTFGGGTKLEIKRA
24B VL    SGVPDRFSGSGSGTDFTLRISRVEAEDLGVYYCWQGTHLPHAFGGGTTLEIKRA
```

Boxed segments each represent a complementarity determining region (CDR).

Figure 9

L2 epitopes recognized by monoclonal antibodies 13B and 24B

```
13B    GGLGIGTGSGTGGRTGYIPL
24B    GGLGIGTGSGTGGRTGYIPL
```

```
                24B       13B
              aa58-67   aa64-73

HPV16  50-SMGVFFGGLGIGTGSGTGGRTGYIPL-75
HPV18  49-*L*I*L*********************-74
HPV31  50-***********S***********V**-75
HPV33  49-*L*************S*******V*I-74
HPV35  50-A******S****SV**-75
HPV39  49-*L*I*L********T*************-74
HPV45  49-*L*I*L***********S*******V**-74
HPV51  49-GL*I*L***********S**********-74
HPV52  49-*L***********A*S*AV**-74
HPV56  49-*LFTY********T*S*AV**-74
HPV58  49-*L***********************V**-74
HPV59  49-*L*I*L*********************-74
HPV66  49-*LFTY*********S*AV-74
HPV68  49-*L*I*L*********************-74
HPV73  51-*I**********S***S*******V**-76
HPV6   49-*L**********************V**-74
HPV11  50-*L***********A*S***A*****-75
HPV2   48-*L***********************V-73
HPV27  47-*L***********************V-72
```

MONOCLONAL ANTIBODY RECOGNIZING HUMAN PAPILLOMAVIRUS (HPV) L2 PROTEIN AND METHOD FOR MEASURING HPV-NEUTRALIZING ANTIBODY TITER USING THE SAME

CROSS-REFERENCE TO RELATED APPLICATIONS

This application is a divisional application of U.S. Ser. No. 13/997,902, filed on Aug. 20, 2013, which is a national stage application, filed under 35 U.S.C. §371, of International Application No. PCT/JP2011/079994, filed Dec. 26, 2011, designating the United States and published in Japanese on Jul. 5, 2012 as publication WO2012/090895. PCT/JP2011/079994 claims priority to Japanese Patent Application Ser. No. 2010-291067, filed Dec. 27, 2010. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 25, 2013, is named 93266_46342_ST25.txt and is 18,045 in size.

TECHNICAL FIELD

The present invention relates to a monoclonal antibody recognizing HPV L2 protein and a method for measuring the antibody titer of cross-neutralizing antibody using the same.

BACKGROUND ART

HPV has more than 100 genotypes. Among genotypes infecting mucosal epithelium (mucosal HPV), at least 15 types (high-risk types 16, 18, 31, 33, 35, 39, 45, 51, 52, 56, 58, 59, 66, 68 and 73) are responsible for uterine cervical cancer.

HPV particles have an icosahedral capsid structure which is composed of 72 pentamers (capsomeres) of L1 protein and 12 molecules of L2 protein and within which DNA genomes are encapsulated. Upon overexpression of L1 protein alone by recombinant DNA technology, a capsid-like structure (L1-capsid) is formed. Upon co-expression with L2 protein, a capsid of the same composition as that of the virus particles is formed (L1/L2-capsid). The L1-capsid has strong immunogenicity and is shown to induce both antibody production and cellular immunity without any adjuvant when inoculated into animals. This immunogenicity is specific to the type of HPV, and immunization with type 16 L1-capsid induces reactions specific to type 16.

When used as a vaccine antigen, the L1-capsid can prevent HPV infection. Vaccines comprising the L1-capsids of HPV types 6, 11, 16 and 18 or HPV types 16 and 18 as antigens have already been developed abroad and are also marketed in Japan. However, these first-generation vaccine antigens are very highly type-specific and, for example, type 16 L1-capsid vaccines prevent only HPV type 16 infection. Thus, there is a demand for the development of a vaccine antigen which induces neutralizing antibodies common to the high-risk types.

The inventors of the present invention have previously found that the L2 protein of HPV type 16 contains type-common neutralization epitopes, and have shown that these epitopes can be used as a next-generation type-common HPV vaccine antigen (Non-patent Document 1, Non-patent Document 2, Non-patent Document 3, and Non-patent Document 4).

Above all, the amino acid sequence of amino acids 56-75 in the HPV16 L2 protein is highly conserved among all high-risk types of HPV, and this region can induce cross-neutralizing antibodies effective against a wide range of types when inoculated into animals in the form of a conjugate with keyhole limpet hemocyanin (KLH) (KLH-P56/75) or in the form of a chimeric capsid composed of a chimeric protein carrying this region inserted into amino acids 430-433 in type 16 L1 protein (16L1-430(56/75) chimeric capsid) (Patent Document 1, Non-patent Document 3, and Non-patent Document 4). As indicated by these findings, antigens having the amino acid sequence of amino acids 56-75 in the L2 protein are promising candidates for use as next-generation HPV vaccines effective against all high-risk types of HPV and are now under development for practical use.

PRIOR ART DOCUMENTS

Patent Documents

Patent Document 1: WO2009/001867

Non-Patent Documents

Non-patent Document 1: Kawana K, et al.: Common neutralization epitope in minor capsid protein L2 of human papillomavirus types 16 and 6. J. Virology, 73, 6188-6190, 1999

Non-patent Document 2: Kawana K, et al.: Safety and immunogenicity of a peptide containing the cross-neutralization epitope of HPV16 L2 administered nasally in healthy volunteers. Vaccine, 21: 4256-4260, 2003

Non-patent Document 3: Kondo K, et al.: Neutralization of HPV16, 18, 31, and 58 pseudovirons with antisera induced by immunizing rabbits with synthetic peptides representing segments of the HPV16 minor capsid protein L2 surface region. Virology, 358: 266-272, 2007

Non-patent Document 4: Kondo K, et al., Modification of human papillomavirus-like particle vaccine by insertion of the cross-reactive L2-epitopes. J. Med. Virol., 80: 841-846, 2008

SUMMARY OF INVENTION

Technical Problem

For practical use of an antigen comprising the amino acid sequence of amino acids 56-75 in the L2 protein as a next-generation HPV vaccine, it is necessary to study whether this antigen efficiently induces cross-neutralizing antibodies in humans. Particularly in clinical trials, a simple and high-throughput method is required to measure cross-neutralizing antibody titers because many serum samples from subjects should be measured.

Since there is no cultured cell line allowing HPV proliferation, an infectious pseudovirus, which is HPV L1/L2-capsid carrying an expression plasmid for a reporter gene or the like is used to monitor HPV infection. Neutralizing antibodies against HPV are assayed by measuring their ability to inhibit infection of this infectious pseudovirus. However, this method cannot distinguish infection inhibition by genotype-specific neutralizing antibody (i.e., antibody against the L1 protein of each HPV) from infection inhibition by cross-neutralizing antibody (i.e., antibody against the L2 protein common to HPV types), and is also not suitable for assay of many analytes because it requires much effort and time.

Under these circumstances, there has been a demand for the development of a high-throughput method for measuring the antibody titer of cross-neutralizing antibody induced by a next-generation HPV vaccine.

Solution to Problem

The inventors of the present invention have prepared a monoclonal antibody against a peptide having a specific amino acid sequence common to the L2 proteins of high-risk type HPVs and have found a method using this monoclonal antibody to assay cross-neutralizing antibodies induced by next-generation HPV vaccines. This finding led to the completion of the present invention.

Namely, the present invention provides the anti-HPV L2 protein monoclonal antibody shown below, a method for assay or diagnosis of cross-neutralizing antibody using the above monoclonal antibody, an assay kit, diagnostic reagent or pharmaceutical preparation comprising the above monoclonal antibody, as well as cells producing the above monoclonal antibody, etc.

[1] A monoclonal antibody, which recognizes a common epitope in human papillomavirus L2 protein.

[2] The monoclonal antibody according to [1] above, wherein the common epitope in human papillomavirus L2 protein consists of the amino acid sequence shown in SEQ ID NO: 2, SEQ ID NO: 3, SEQ ID NO: 24 or SEQ ID NO: 25.

[3] The monoclonal antibody according to [1] above, wherein the common epitope in human papillomavirus L2 protein consists of the amino acid sequence shown in SEQ ID NO: 2 or SEQ ID NO: 3.

[4] The monoclonal antibody according to [1] above, which comprises the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3).

[5] The monoclonal antibody according to [1] above, which comprises the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3).

[6] The monoclonal antibody according to [1] above, whose heavy chain variable region is the amino acid sequence shown in SEQ ID NO: 7 and whose light chain variable region is the amino acid sequence shown in SEQ ID NO: 8.

[7] The monoclonal antibody according to [1] above, whose heavy chain variable region is the amino acid sequence shown in SEQ ID NO: 9 and whose light chain variable region is the amino acid sequence shown in SEQ ID NO: 10.

[8] The monoclonal antibody according to [6] above, which recognizes human papillomavirus L2 protein and is produced by a hybridoma cell line of accession No. FERM BP-11304.

[9] The monoclonal antibody according to [7] above, which recognizes human papillomavirus L2 protein and is produced by a hybridoma cell line of accession No. FERM BP-11305.

[10] A method for measuring the antibody titer of cross-neutralizing antibody against human papillomavirus (HPV), which comprises the steps of:

(a) bringing a test sample into contact with an HPV antigen to establish binding of antibodies in the sample to the antigen; and (b) adding the monoclonal antibody according to [1] above to the reaction system in step (a) to determine the amount of the monoclonal antibody bound to the antigen.

[11] A method for measuring the antibody titer of cross-neutralizing antibody against human papillomavirus (HPV), which comprises the steps of:

(a) bringing a test sample into contact with an HPV antigen to establish binding of antibodies in the sample to the antigen; and (b) bringing the residual epitopes, which remain unbound to the antibodies in step (a), into contact with the monoclonal antibody according to [1] above to determine the amount of the monoclonal antibody bound to the epitopes.

[12] A method for measuring the antibody titer of cross-neutralizing antibody against human papillomavirus (HPV), which comprises the steps of:

(a) bringing the monoclonal antibody according to [1] above in admixture with a test sample into contact with an HPV antigen to form antibody/antigen conjugates; and (b) determining the amount of the monoclonal antibody used to form antibody/antigen conjugates among those obtained in step (a).

[13] The method according to [10] or [11] above, wherein the monoclonal antibody bound to the antigen or the monoclonal antibody contacted with and hence bound to the epitopes is further contacted with a labeled secondary antibody recognizing the monoclonal antibody, and the intensity of signals arising from the labeled secondary antibody is measured in the presence and absence of the test sample to thereby determine the antibody titer of possible cross-neutralizing antibody in the test sample.

[14-1] The method according to [12] above, wherein the conjugates formed between the monoclonal antibody and the antigen in step (a) are contacted with a labeled secondary antibody recognizing the monoclonal antibody, and the intensity of signals arising from the labeled secondary antibody is measured before and after addition of the test sample to thereby determine the antibody titer of possible cross-neutralizing antibody in the test sample.

[14-2] The method according to [12] above, wherein the conjugates formed between the monoclonal antibody and the antigen in step (a) are contacted with a labeled secondary antibody recognizing the monoclonal antibody, and the intensity of signals arising from the labeled secondary antibody is measured in the presence and absence of the test sample to thereby determine the antibody titer of possible cross-neutralizing antibody in the test sample.

[15] The method according to any one of [10] to [14-2] above, wherein the HPV antigen is immobilized on a solid support.

[16] A kit for determining the presence of cross-neutralizing antibody against HPV in a test sample, which comprises (a) an HPV antigen immobilized on a solid support, (b) the monoclonal antibody according to [1] above, and (c) a labeled secondary antibody recognizing the monoclonal antibody according to [1] above.

[17] A diagnostic reagent for HPV infection, which comprises the monoclonal antibody according to [1] above.

[18] A cell line, which produces the monoclonal antibody according to [1] above.

[19] The cell line according to [18] above, whose accession No. is FERM BP-11304 or FERM BP-11305.

[20] A pharmaceutical preparation, which comprises the monoclonal antibody according to [1] above.

[21] A therapeutic agent for HPV, which comprises the monoclonal antibody according to [1] above.

Advantageous Effects of Invention

According to the present invention, binding between the monoclonal antibody of the present invention and an HPV antigen can be determined from the degree of competitive inhibition with a sample to thereby know cross-neutralizing antibody levels in the sample. Because of using ELISA, the method of the present invention is rapid and simple, and allows high-throughput measurement of cross-neutralizing antibody titers in many serum samples obtained from subjects during clinical trials. Moreover, the monoclonal antibody of the present invention can also be used for diagnosis of HPV infection or used as a therapeutic agent for HPV infection.

BRIEF DESCRIPTION OF DRAWINGS

FIG. 2 shows epitopes in P56/75 recognized by monoclonal antibodies 13B and 24B, along with amino acid sequence regions conserved among high-risk types of HPV (SEQ ID NOs 1, 34 to 36, 44, 37 to 43, 45, and 46 to 50).

FIG. 7 shows the amino acid sequences of heavy and light chain variable regions in monoclonal antibodies 13B and 24B (SEQ ID NOs: 7 to 10), along with their complementarity determining regions (CDRs) (SEQ ID NOs: 11 to 22).

FIG. 9 shows epitopes in P56/75 recognized by monoclonal antibodies 13B and 24B, along with amino acid sequence regions conserved among high-risk types of HPV (SEQ ID NOs: 1 and 34 to 52).

DESCRIPTION OF EMBODIMENTS

Figure 1:
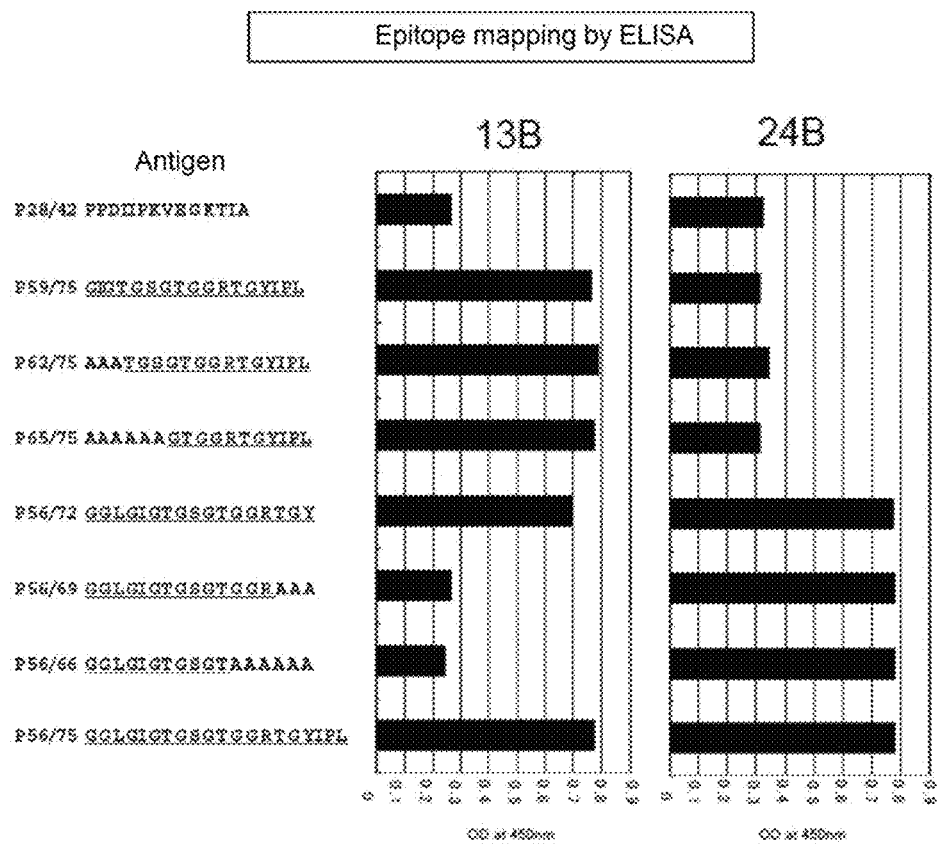
FIG. 1 shows the results of epitope mapping by ELISA (SEQ ID NOs 53 to 59 and 1).

An explanation will be given below of how to prepare an antigen for a monoclonal antibody recognizing HPV L2 protein (hereinafter also referred to as the monoclonal antibody of the present invention) and how to prepare such a monoclonal antibody.

Human papillomavirus has two structural genes L1 and L2, and their products function as capsid proteins.

The term "human papillomavirus L2 protein" is intended to mean a protein encoded by the L2 gene of human papillomavirus (HPV) (Zhou J et al., Expression of vaccinia recombinant HPV 16 L1 and L2 ORF proteins in epithelial cells is sufficient for assembly of HPV virion-like particles. Virology. 185: 251-257, 1991).

The HPV L2 protein or L2 peptide used in the present invention may be, for example, a protein (polypeptide) represented by GGLGIGTGSGTGGRTGYIPL (SEQ ID NO: 1) or a derivative thereof.

Examples of derivatives of a polypeptide having the amino acid sequence shown in SEQ ID NO: 1 include (1) those comprising deletion of one or more (preferably around 1 to 10, more preferably several (1 to 9 or 1 to 5), even more preferably 1, 2 or 3) amino acids from the above amino acid sequence, (2) those comprising addition of one or more (preferably around 1 to 20, more preferably around 1 to 10, even more preferably several (1 to 9), still even more preferably 1, 2 or 3) amino acids to the above amino acid sequence, (3) those comprising insertion of one or more (preferably around 1 to 20, more preferably around 1 to 10, even more preferably several (1 to 9), still even more preferably 1, 2 or 3) amino acids into the above amino acid sequence, or (4) those comprising substitution of other amino acids for one or more (preferably around 1 to 10, more preferably several (1 to 9 or 1 to 5), even more preferably 1, 2 or 3) amino acids in the above amino acid sequence, or (5) any combination thereof.

It should be noted that in the protein (polypeptide) notation used herein, the left-hand direction is the N-terminal (amino terminal) direction and the right-hand direction is the C-terminal (carboxyl terminal) direction, in accordance with standard usage and convention.

The protein used in the present invention may have any group selected from carboxyl, carboxylate, amido or ester at the C-terminal end.

As used herein, the term "antibody" is intended to mean a whole antibody molecule or a fragment thereof, which is capable of recognizing or binding to HPV L2 protein serving as an antigen. It may be either polyclonal or monoclonal.

As used herein, the term "monoclonal antibody" refers to an antibody molecule obtained from a single type of antibody-producing cells. The term "monoclonal antibody" encompasses monoclonal antibody molecules per se or fragments thereof.

A "fragment" of the above antibody or monoclonal antibody refers to a part of the full-length antibody, generally a portion including an antigen-binding region or a variable region. For example, antibody fragments include Fab, Fab', F(ab')2 and Fv fragments. Other fragments include diabodies, linear antibodies, single chain antibody molecules, and multispecific antibodies composed of antibody fragments.

A preferred monoclonal antibody used in the method of the present invention is IgG1 or IgG2 antibody, which comprises light chain and heavy chain variable regions of mouse origin, and γ1 heavy chain and κ light chain constant regions of mouse origin.

Moreover, preferred for use as a pharmaceutical preparation is a monoclonal antibody which is partially or completely humanized or which is chimeric, as described later.

As used herein, the term "common epitope" is intended to mean a region in the amino acid sequence of HPV L2 protein, which is highly conserved among high-risk types of HPV and can be recognized by the monoclonal antibody of the present invention, as exemplified by the amino acid sequence GTGGRTGYIPL (SEQ ID NO: 2), GGLGIGTGS-GTGGR (SEQ ID NO: 3), SGTGGRTGYI (SEQ ID NO: 24) or LGIGTGSGTG (SEQ ID NO: 25) or the amino acid sequence GTGGRTGYIPL (SEQ ID NO: 2) or GGL-GIGTGSGTGGR (SEQ ID NO: 3), or mutated sequences thereof.

Polypeptides having mutated sequences of the amino acid sequences shown in SEQ ID NO: 2, SEQ ID NO: 3, SEQ ID NO: 24 and SEQ ID NO: 25 include (1) those comprising deletion of 1 to 3 (or 1 to 2, or 1) amino acids from the above amino acid sequences, (2) those comprising addition of 1 to 3 (or 1 to 2, or 1) amino acids to the above amino acid sequences, (3) those comprising insertion of 1 to 3 (or 1 to 2, or 1) amino acids into the above amino acid sequences, or (4) those comprising substitution of other amino acids for 1 to 3 (or 1 to 2, or 1) amino acids in the above amino acid sequences, or (5) any combination thereof.

As used herein, the phrase "recognizing HPV L2 protein" is intended to mean specifically binding to HPV L2 protein, and more specifically intended to mean that specific antigen-antibody reaction can be detected by an immunoassay such as enzyme immunoassay.

The monoclonal antibody recognizing HPV L2 protein according to the present invention may be of any type as long as it specifically binds to a partial peptide of the HPV L2 protein (preferably HPV L2 peptide (P56/75) of SEQ ID NO: 1). Examples of such a monoclonal antibody include those specifically binding to a polypeptide having the amino acid sequence shown in SEQ ID NO: 1 or a derivative thereof.

More specific examples of the monoclonal antibody recognizing HPV L2 protein according to the present invention include those specifically binding to a common epitope in the HPV L2 protein (preferably the peptide of SEQ ID NO: 2, SEQ ID NO: 3, SEQ ID NO: 24 or SEQ ID NO: 25).

The monoclonal antibody recognizing the peptide of SEQ ID NO: 2 is herein referred to as 13B, while the monoclonal antibody recognizing the peptide of SEQ ID NO: 3 is herein referred to as 24B. 13B also encompasses a monoclonal antibody recognizing the peptide of SEQ ID NO: 24. 24B also encompasses a monoclonal antibody recognizing the peptide of SEQ ID NO: 25.

As used herein, the term "complementarity determining region" is intended to mean a region in the variable region, which directly binds to an antigen in a complementary manner, and more specifically refers to three regions (CDRH1, CDRH2 and CDRH3, or CDRL1, CDRL2 and CDRL3) in the heavy or light chain shown in FIG. 7.

A preferred monoclonal antibody is monoclonal antibody 13B or 24B whose complementarity determining regions (CDRs) have the sequences of CDR1 to CDR3 in the heavy and light chains shown in FIG. 7.

More preferred is a monoclonal antibody whose heavy chain variable region is the amino acid sequence shown in SEQ ID NO: 7 and whose light chain variable region is the amino acid sequence shown in SEQ ID NO: 8, wherein the amino acid sequences shown in SEQ ID NOs: 7 and 8 may be mutated sequences thereof, except for their complementarity determining regions. Such a complementarity determining region is, for example, the amino acid sequence shown in at least one of SEQ ID NOs: 11 to 16.

Alternatively preferred is a monoclonal antibody whose heavy chain variable region is the amino acid sequence shown in SEQ ID NO: 9 and whose light chain variable region is the amino acid sequence shown in SEQ ID NO: 10, wherein the amino acid sequences shown in SEQ ID NOs: 9 and 10 may be mutated sequences thereof, except for their complementarity determining regions. Such a complementarity determining region is, for example, the amino acid sequence shown in at least one of SEQ ID NOs: 17 to 22.

Mutated sequences of the amino acid sequences shown in SEQ ID NOs: 7 to 10, except for their complementarity determining regions, include (1) those comprising deletion of one or more (preferably around 1 to 10, more preferably several (1 to 9 or 1 to 5), even more preferably 1, 2 or 3) amino acids from the above amino acid sequences, (2) those comprising addition of one or more (preferably around 1 to 20, more preferably around 1 to 10, even more preferably several (1 to 9), still even more preferably 1, 2 or 3) amino acids to the above amino acid sequences, (3) those comprising insertion of one or more (preferably around 1 to 20, more preferably around 1 to 10, even more preferably several (1 to 9), still even more preferably 1, 2 or 3) amino acids into the above amino acid sequences, or (4) those comprising substitution of other amino acids for one or more (preferably around 1 to 10, more preferably several (1 to 9 or 1 to 5), even more preferably 1, 2 or 3) amino acids in the above amino acid sequences, or (5) any combination thereof.

The amino acid sequences of constant regions may be those derived from human or mammalian (e.g., mouse, rat, rabbit, sheep, pig, bovine, cat, dog, monkey) IgG1 or IgG2 antibody.

Examples of monoclonal antibody 13B include monoclonal antibody produced from hybridoma cells indicated as Mouse-Mouse hybridoma 13B (FERM BP-11304). Examples of monoclonal antibody 24B include monoclonal antibody produced from hybridoma cells indicated as Mouse-Mouse hybridoma 24B (FERM BP-11305).

The term "cross-neutralizing antibody" is intended to mean an antibody capable of neutralizing two or more genotypes of HPV or an antibody capable of neutralizing infection of two or more genotypes of HPV. HPV is known to have a very large number of genotypes, such as types 6, 11, 16, 18, 31, 33, 35, 39, 45, 51, 52, 56, 58, 59, 66, 68 and 73 (zur Hausen H. Papillomavirus infections—a major cause of human cancers. Biochim Biophys Acta. 1288: F55-78, 1996). A preferred cross-neutralizing antibody is an antibody capable of neutralizing three or more high-risk types of HPV (types 16, 18, 31, 33, 35, 39, 45, 51, 52, 56, 58, 59, 66, 68 and 73). More preferred is an antibody capable of neutralizing types 16 and 18 as well as at least one or more types of HPV selected from types 33, 52 and 58. More specifically, preferred is an antibody specifically binding to the L2 proteins of the above high-risk types of HPV and capable of neutralizing HPV.

The term "HPV antigen" is intended to mean an antigen used to form an antigen/antibody conjugate during assay of cross-neutralizing antibody. HPV antigens which can be used may be of any genotype as long as they have a type-common epitope (e.g., a common epitope), as exemplified by capsids or pseudoviruses carrying the L2 protein. Preferred is an L1/L2 chimeric capsid of HPV16. Moreover, it is also possible to use, as an HPV antigen, the full-length L2 peptide or a part thereof (e.g., L2 peptide (56-75)) or a mutant thereof or the L2 peptide conjugated with keyhole limpet hemocyanin (e.g., KLH-P56/75) or with BSA, etc.

The term "labeled secondary antibody" is intended to mean an antibody recognizing the monoclonal antibody of the present invention, which is labeled with a substance capable of generating detectable signals such as enzyme activity, radioisotope, color development or luminescence.

An explanation will be given below of how to prepare an antigen for the monoclonal antibody of the present invention and how to prepare the monoclonal antibody of the present invention.

(1) Antigen Preparation

Any antigen may be used to prepare the monoclonal antibody of the present invention, as exemplified by a peptide having a sequence covering amino acids 56-75 in HPV L2 protein (L2 peptide (56-75)), more specifically a (synthetic) peptide having one or more antigenic determinants which are the same as those of a polypeptide containing the amino acid sequence shown in SEQ ID NO: 1 or a salt thereof, as well as a polypeptide consisting of the amino acid sequence shown in SEQ ID NO: 1 or a derivative thereof (which are also simply referred to as L2 peptide antigens).

A polypeptide containing the amino acid sequence shown in SEQ ID NO: 1 or a salt thereof can be prepared in a known manner, for example, according to the method described in WO 09/01867. Moreover, a peptide for use as an L2 peptide antigen can also be prepared (1) according to known techniques for peptide synthesis or (2) by cleaving a polypeptide containing the amino acid sequence shown in SEQ ID NO: 1 or SEQ ID NO: 2, 3, 24 or 25 with an appropriate peptidase(s).

Techniques for peptide synthesis may be either solid phase synthesis techniques or liquid phase synthesis techniques. Namely, a partial peptide or amino acids capable of constituting such a peptide are condensed with the remainder part and, if the product has protective groups, these protective groups are eliminated, whereby a desired peptide can be prepared. Procedures known for condensation and elimination of protective groups can be found in the following documents, by way of example:
(i) M. Bodanszky and M. A. Ondetti, Peptide Synthesis, Interscience Publishers, New York (1966); and
(ii) Schroeder and Luebke, The Peptide, Academic Press, New York (1965).

After reaction, the peptide can be purified and isolated by standard procedures for purification, such as solvent extraction, distillation, column chromatography, liquid chromatography and recrystallization, which are used in combination. If the peptide thus obtained is in a free form, it can be converted into an appropriate salt form in a known manner. Conversely, if the peptide is obtained in a salt form, it can be converted into a free form in a known manner.

An amide form of a peptide can be synthesized using a commercially available peptide synthesis resin suitable for amide formation. Examples of such a resin include chloromethyl resin, hydroxymethyl resin, benzhydrylamine resin, aminomethyl resin, 4-benzyloxybenzylalcohol resin, 4-methylbenzhydrylamine resin, PAM resin, 4-hydroxymethylmethylphenylacetamidemethyl resin, polyacrylamide resin, 4-(2',4'-dimethoxyphenyl-hydroxymethyl)phenoxy resin, 4-(2',4'-dimethoxyphenyl-Fmoc aminoethyl)phenoxy resin, etc. Using such a resin, amino acids whose α-amino group and side chain functional group(s) are appropriately protected are condensed on the resin in line with the sequence of a desired peptide according to various known condensation techniques. In the final step of the reaction, a peptide is cleaved off from the resin simultaneously with removing the various protective groups to thereby obtain a desired peptide. Alternatively, chlorotrityl resin, oxime resin, 4-hydroxybenzoic acid resin or the like is used for synthesis and a partially protected peptide is cleaved off and treated in a routine manner to remove the protective groups, whereby a desired peptide can be obtained.

For condensation of protected amino acids as described above, it is possible to use various activating reagents which can be used for peptide synthesis, and particularly preferred is carbodiimides. Examples of carbodiimides include DCC, N,N'-diisopropylcarbodiimide, N-ethyl-N'-(3-dimethylaminoprolyl)carbodiimide and so on. For activation with these reagents, protected amino acids may be directly added to the resin together with a racemization-inhibiting additive (e.g., HOBt, HOOBt), or may be activated as symmetric acid anhydrides or as HOBt esters or as HOOBt esters before being added to the resin. A solvent used for activation of protected amino acids or their condensation with the resin may be selected as appropriate from among solvents known to be usable for peptide condensation reaction. Examples include acid amides (e.g., N,N-dimethylformamide, N,N-dimethylacetamide, N-methylpyrrolidone), halogenated hydrocarbons (e.g., methylene chloride, chloroform), alcohols (e.g., trifluoroethanol), sulfoxides (e.g., dimethyl sulfoxide), tertiary amines (e.g., pyridine), ethers (e.g., dioxane, tetrahydrofuran), nitriles (e.g., acetonitrile, propionitrile), esters (e.g., methyl acetate, ethyl acetate) or appropriate mixtures thereof. The reaction temperature may be selected as appropriate from the range known to be usable for peptide bond formation reaction, generally selected as appropriate from the range of about −20° C. to about 50° C. Activated amino acid derivatives are generally used in about 1.5-fold to about 4-fold excess. If condensation is not sufficient as tested by ninhydrin reaction, the condensation reaction may be repeated without eliminating protective groups to thereby ensure sufficient condensation. If sufficient condensation is not achieved even by repeating the reaction, unreacted amino acids may be acetylated with acetic anhydride or acetylimidazole to thereby avoid any influence on the subsequent reactions.

Protective groups for amino groups in starting amino acids may be exemplified by a benzyloxycarbonyl group, a t-butoxycarbonyl group, a t-pentyloxycarbonyl group, an isobornyloxycarbonyl group, a 4-methoxybenzyloxycarbonyl group, a 2-Cl-benzyloxycarbonyl group, a 2-Br-benzyloxycarbonyl group, an adamantyloxycarbonyl group, a trifluoroacetyl group, a phthaloyl group, a formyl group, a 2-nitrophenylsulfenyl group, a diphenylphosphinothioyl group, a N-9-fluorenylmethoxycarbonyl group, etc. Protective groups for carboxyl groups may be exemplified by a $C_{1-6}$ alkyl group, a $C_{3-8}$ cycloalkyl group, a $C_{7-14}$ aralkyl group, a 2-adamantyl group, a 4-nitrobenzyl group, a 4-methoxybenzyl group, a 4-chlorobenzyl group, a phenacyl group and a benzyloxycarbonylhydrazide group, a t-butoxycarbonylhydrazide group, a tritylhydrazide group, etc.

Hydroxyl groups in serine and threonine may be protected, for example, by esterification or etherification. Examples of groups suitable for esterification in this case include a lower ($C_{1-6}$) alkanoyl group (e.g., an acetyl group), an aroyl group (e.g., a benzoyl group), a carbonic acid-derived group (e.g., a benzyloxycarbonyl group, an ethoxycarbonyl group), etc. Likewise, examples of groups suitable for etherification include a benzyl group, a tetrahydropyranyl group, a t-butyl group, etc.

Examples of a protective group for the phenolic hydroxyl group in tyrosine include a benzyl group, a Cl-benzyl group, a 2-nitrobenzyl group, a Br-benzyloxycarbonyl group, a t-butyl group, etc.

Examples of a protective group for the imidazole in histidine include a p-toluenesulfonyl group, a 4-methoxy-2, 3,6-trimethylbenzenesulfonyl group, a dinitrophenol group, a benzyloxymethyl group, a t-butoxymethyl group, a t-butoxycarbonyl group, a trityl group, a N-9-fluorenylmethoxycarbonyl group, etc.

Activated forms of carboxyl groups in starting materials may be exemplified by corresponding acid anhydrides, azides, active esters [esters with alcohols (e.g., pentachlorophenol, 2,4,5-trichlorophenol, 2,4-dinitrophenol, cyanomethyl alcohol, paranitrophenol, HONB, N-hydroxysuccinimide, N-hydroxyphthalimide, HOBt)], etc. Activated forms of amino groups in starting materials may be exemplified by corresponding phosphoric amides.

Techniques for removal (elimination) of protective groups include, for example, catalytic reduction in a hydrogen stream in the presence of a catalyst (e.g., Pd-black or Pd-carbon); acid treatment with anhydrous hydrogen fluoride, methanesulfonic acid, trifluoromethanesulfonic acid, trifluoroacetic acid or a mixture thereof, etc.; base treatment with diisopropylethylamine, triethylamine, piperidine, piperazine, etc.; as well as reduction with sodium in liquid ammonia. Elimination reaction by the above acid treatment is generally performed at a temperature of −20° C. to 40° C., and addition of a cation trapping agent (e.g., anisole, phenol, thioanisole, metacresol, paracresol, dimethyl sulfide, 1,4-butanedithiol, 1,2-ethanedithiol) is effective for acid treatment. Likewise, a 2,4-dinitrophenyl group used as a protective group for the imidazole in histidine may be removed by thiophenol treatment, while a formyl group used as a protective group for the indole in tryptophan may be removed not only by deprotection through acid treatment in the presence of 1,2-ethanedithiol or 1,4-butanedithiol as mentioned above, but also by alkaline treatment with dilute sodium hydroxide, dilute ammonia, etc.

Protection of and protective groups for functional groups in starting materials, which should not be involved in reactions, as well as elimination of the protective groups and activation of functional groups involved in reactions may be selected as appropriate from among known groups or known means.

Another technique for obtaining an amide form of a peptide is as follows. First, the α-carboxyl group in the carboxyl terminal amino acid is amidated, and the peptide chain is then extended from the amino group side to a desired chain length, followed by preparing a peptide from this peptide chain by removing only the protective group on the α-amino group at the N-terminal end and a peptide (or an amino acid) by removing only the protective group on the C-terminal carboxyl group, both of which peptides are further condensed in a mixed solvent as mentioned above. The details of condensation reaction are as described above. After the protected peptide obtained by condensation is purified, all the protective groups are removed in the manner described above to obtain a desired crude peptide. This crude peptide is purified with full use of various known purification techniques and its major fractions are lyophilized, whereby an amide form of the desired peptide can be obtained.

To obtain an ester form of a peptide, the α-carboxyl group in the carboxy terminal amino acid is condensed with a desired alcohol to give an amino acid ester, followed by repeating the same procedure as used to obtain an amide form of a peptide, whereby an ester form of a desired peptide can be obtained.

An L2 peptide antigen may be directly used for immunization. Alternatively, an L2 peptide antigen may also be conjugated with or adsorbed onto an appropriate carrier for use in immunization. The carrier may be of any type and may be mixed with the L2 peptide antigen (hapten) at any ratio for conjugation or adsorption as long as monoclonal antibody can be efficiently induced against the L2 peptide antigen conjugated with or adsorbed onto the carrier. In general, a natural or synthetic polymeric carrier, which is commonly used for preparation of monoclonal antibody against a hapten antigen, may be used for conjugation or adsorption at a weight ratio of 0.1 to 100 per hapten. Examples of a natural polymeric carrier available for use include mammalian serum albumin (e.g., bovine, rabbit or human serum albumin), mammalian thyroglobulin (e.g., bovine or rabbit thyroglobulin), mammalian hemoglobin (e.g., bovine, rabbit, human or sheep hemoglobin), keyhole limpet hemocyanin, etc. Examples of a synthetic polymeric carrier available for use include various latexes of polymers or copolymers such as polyamino acids, polystyrenes, polyacryls, polyvinyls, polypropylenes, etc.

Moreover, various condensing agents may be used for coupling between hapten and carrier. Examples of condensing agents advantageous for use include diazonium compounds (e.g., bisdiazotized benzidine) which allow crosslinking of tyrosine, histidine or tryptophan; dialdehyde compounds (e.g., glutaraldehyde) which allow crosslinking between amino groups; diisocyanate compounds (e.g., toluene-2,4-diisocyanate); dimaleimide compounds (e.g., N,N'-o-phenylenedimaleimide) which allow crosslinking between thiol groups; maleimide active ester compounds which allow crosslinking between amino group and thiol group; carbodiimide compounds which allow crosslinking between amino group and carboxyl group, etc. Moreover, for crosslinking between amino groups, one of the amino groups may be reacted with an active ester reagent having a dithiopyridyl group (e.g., 3-(2-pyridyldithio)propionic acid N-succinimidyl (SPDP)) and then reduced to thereby introduce a thiol group, while the other amino group may be treated with a maleimide active ester reagent to introduce a maleimide group, followed by reaction of both amino groups.

In the preparation of the monoclonal antibody of the present invention, an L2 peptide antigen as described above is preferably conjugated with KLH (keyhole limpet hemocyanin). It should be noted that a preferred conjugate between KLH and L2 peptide antigen has an additional cysteine residue at the N-terminal end to avoid masking of the peptide region with this KLH.

(2) Monoclonal Antibody Preparation

An L2 peptide antigen is administered alone or in combination with a carrier or diluent to warm-blooded animals at a site where antibody production is possible, for example, by intraperitoneal infusion, intravenous infusion, intracutaneous injection, subcutaneous injection or other modes of administration. To enhance antibody productivity, complete Freund's adjuvant or incomplete Freund's adjuvant may be administered during antigen administration. The administration is generally repeated once every 2 to 6 weeks and twice to 10 times in total. Examples of warm-blooded animals include monkeys, rabbits, dogs, guinea pigs, mice, rats, sheep, goats, chickens and so on, with mice being preferred for use in monoclonal antibody preparation.

For monoclonal antibody preparation, among the warm-blooded animals (e.g., mice) immunized with the L2 peptide antigen, those showing antibody titers are selected and their spleens or lymph nodes are taken at 2 to 5 days after the final immunization. Antibody-producing cells contained in these spleens or lymph nodes may be fused with myeloma cells to thereby prepare a hybridoma producing the monoclonal antibody of the present invention (hereinafter also referred to as the antibody-producing hybridoma of the present invention).

Anti-L2 peptide antibody titers in serum may be determined, for example, by reacting a labeled L2 peptide as described later with an antiserum sample and then measuring the activity of the label bound to antibody molecules. Cell fusion may be accomplished in a known manner, for example, according to the method of Miler and Milstein [Nature, vol. 256, page 495 (1975)]. Examples of a fusion promoter include polyethylene glycol (PEG), Sendai virus and so on, with PEG or the like being preferred for use. Examples of myeloma cells include NS-1, P3U1, SP2/0, AP-1 and so on, with P3U1 or the like being preferred for use. A preferred ratio between antibody-producing cells (spleen cells) and myeloma cells to be used is usually around 1:1 to 20:1, and PEG (preferably PEG1000 to PEG6000) is added at a concentration of about 10% to 80% and incubation is continued usually at 20° C. to 40° C., preferably 30° C. to 37° C., usually for 1 to 10 minutes to thereby achieve efficient cell fusion.

For screening of the antibody-producing hybridoma of the present invention, various techniques can be used. For example, hybridoma culture supernatants are each added to a solid phase (e.g., a microplate) on which a polypeptide containing the amino acid sequence shown in SEQ ID NO: 1 or a salt thereof or a partial peptide thereof is adsorbed directly or in combination with a carrier, followed by addition of radioactively or enzymatically labeled anti-immunoglobulin antibody (anti-mouse immunoglobulin antibody is used when the antibody-producing cells used for cell fusion are of mouse origin) or Protein A to detect the antibody of the present invention bound to the solid phase. Alternatively, hybridoma culture supernatants are each added to a solid phase on which anti-immunoglobulin antibody or Protein A is adsorbed, followed by addition of a radioactively or enzymatically labeled polypeptide containing the amino acid sequence shown in SEQ ID NO: 1 to detect the monoclonal antibody of the present invention bound to the solid phase. In the above screening, HPV16 L1/L2 capsid may also be used as an antigen. Screening or breeding of hybridomas producing the monoclonal antibody of the present invention is generally accomplished in the presence of HAT (hypoxanthine, aminopterin, thymidine) in a medium for animal cells (e.g., RPMI1640) containing 10% to 20% fetal bovine serum. The antibody titer of each hybridoma culture supernatant can be measured in the same manner as described above for measurement of the antibody titer of the antibody of the present invention in antiserum.

The monoclonal antibody of the present invention can be obtained from a cultured product (e.g., culture supernatant, cultured cells) of the antibody-producing hybridoma of the present invention. Alternatively, the monoclonal antibody of the present invention can also be obtained from a body fluid (e.g., ascites, blood) of non-human warm-blooded animals inoculated in vivo (e.g., intraperitoneally) with the antibody-producing hybridoma of the present invention. As in the case of standard separation and purification of polyclonal antibodies, the monoclonal antibody of the present invention may be separated and purified from such a cultured product or body fluid according to separation and purification techniques for immunoglobulins [e.g., salting-out method, alcohol precipitation, isoelectric point precipitation, electrophoresis, adsorption/desorption with an ion exchanger (e.g., DEAE), ultracentrifugation, gel filtration, specific purification techniques in which an antigen-immobilized solid phase or an active adsorbent (e.g., Protein A or Protein G) is used to collect only monoclonal antibody molecules, which are then dissociated to obtain the monoclonal antibody molecules].

As described above, the monoclonal antibody of the present invention can be obtained by culturing hybridoma cells inside or outside the body of warm-blooded animals and collecting monoclonal antibody molecules from their body fluids or cultured products.

It should be noted that (a) hybridomas producing the monoclonal antibody of the present invention which is reactive with a partial region of a polypeptide containing the amino acid sequence shown in SEQ ID NO: 1, and (b) hybridomas producing the monoclonal antibody of the present invention which is reactive with the above polypeptide but not with the partial region thereof may be screened, for example, by measuring the binding between a peptide corresponding to the partial region and a monoclonal antibody produced by each hybridoma.

(3) Assay of Cross-Neutralizing Antibody

The monoclonal antibody of the present invention allows efficient assay or detection of cross-neutralizing antibody, preferably efficient assay or detection of the antibody titer of cross-neutralizing antibody against human papillomavirus (HPV).

More specifically, assay may be accomplished by:

Method A, which comprises the steps of:

(a) bringing a test sample into contact with an HPV antigen to establish binding of antibodies in the sample to the antigen; and (b) bringing the residual epitopes, which remain unbound to the antibodies in step (a), into contact with the monoclonal antibody of the present invention to determine the amount of the monoclonal antibody bound to the epitopes; or Method B, which comprises the steps of:

(a) bringing a test sample in admixture with the monoclonal antibody of the present invention into contact with an HPV antigen to form antibody/antigen conjugates; and (b) determining the amount of the monoclonal antibody of the present invention used to form antibody/antigen conjugates among those obtained in step (a).

Alternatively, Method A may comprise the steps of:

(a) bringing a test sample into contact with an HPV antigen to establish binding of antibodies in the sample to the antigen; and (b) adding the monoclonal antibody of the present invention to the reaction system in step (a) to determine the amount of the monoclonal antibody bound to the antigen.

A further explanation will be given below of the assay of cross-neutralizing antibody according to the present invention.

The monoclonal antibody of the present invention may be used in any type of assay. The assay where the amount of the monoclonal antibody of the present invention corresponding to the amount of cross-neutralizing antibody in a test solution can be detected by chemical or physical means and then calculated from standard solutions containing known amounts of antibody is preferred for use.

The method of the present invention uses the monoclonal antibody recognizing a common epitope in HPV L2 protein according to the present invention and is intended to determine the antibody titer of a sample based on the amount of the antibody bound to the HPV antigen. Thus, the method of the present invention can measure the antibody titer of cross-neutralizing antibody against HPV, which recognizes the common epitope.

Details are as follows.

In the case of using Method A, for assay of type-common epitope-recognizing antibody in a test sample, a fixed amount of antigen is contacted with serial dilutions of the sample to establish binding of antibodies in the sample to the antigen, followed by adding a sufficient amount of the monoclonal antibody of the present invention to determine the amount of the monoclonal antibody of the present invention bound to the antigen. In this case, a sufficient amount of the monoclonal antibody of the present invention is intended to mean an amount of the monoclonal antibody equal to or greater than the total amount of the monoclonal antibody which can be bound to epitopes present in the reaction system. It may be determined from the amount of HPV antigen used in the assay and the antibody titer. The monoclonal antibody of the present invention added to the reaction system in step (a) is contacted with and bound to the residual epitopes. As used herein, the term "residual epitopes" is intended to mean HPV antigen epitopes which are not bound to antibody molecules in the sample or HPV antigen epitopes which remain after excluding the epitopes bound to antibody molecules in the sample from all the epitopes present in the reaction system. The monoclonal antibody of the present invention can bind to its recognizable epitopes among the contacted epitopes. The monoclonal antibody of the present invention bound to the antigen may be that bound to antigen molecules to which antibody molecules in the test sample are not bound in step (a) or may be that bound to antigen molecules by being displaced with antibody molecules in the sample. The amount of the monoclonal antibody of the present invention bound to the antigen may be determined, for example, by bringing a labeled secondary antibody recognizing the monoclonal antibody into contact with the monoclonal antibody (e.g., the monoclonal antibody contacted with the residual epitopes) and measuring the intensity of signals arising from the labeled secondary antibody. This method indicates the maximum dilution of the sample which is sufficient to occupy epitopes, i.e., bind to all epitopes in the reaction system. For example, signal intensity may be compared between the presence and absence of the test sample to thereby determine the antibody titer of possible cross-neutralizing antibody in the test sample. Signal intensity in the absence of the test sample may be measured by replacing the test sample in step (a) with a sample (e.g., water, buffer, blood) capable of serving as a negative control.

In the case of using Method B, for assay of type-common epitope-recognizing antibody in a test sample, serial dilutions of the sample are each mixed with a fixed amount of the monoclonal antibody of the present invention, and each mixture is then reacted with a fixed amount of antigen to form antibody/antigen conjugates, followed by determining the amount of the monoclonal antibody of the present invention bound to the antigen. For example, the amount of the monoclonal antibody of the present invention bound to the antigen may be determined by bringing the conjugates formed between the monoclonal antibody of the present invention and the antigen into contact with a labeled secondary antibody recognizing the monoclonal antibody and measuring the intensity of signals arising from the labeled secondary antibody. This method indicates the maximum dilution of the sample which inhibits binding of the monoclonal antibody of the present invention through competitive binding (based on a reference value predetermined for inhibition). For example, signal intensity may be compared between the presence and absence of the test sample or between before and after addition of the test sample to thereby determine the antibody titer of possible cross-neutralizing antibody in the test sample. Signal intensity in the absence of the test sample may be measured by replacing the test sample in step (a) with a sample (e.g., water, buffer, blood) capable of serving as a negative control.

As used herein, the term "antibody titer" is intended to mean an index of antibody's binding strength to its antigen or an index of antibody levels in a sample. In the method of the present invention, antibody titer may be determined as a dilution factor. A reference point is predetermined for the bound amount of the monoclonal antibody of the present invention, and the dilution factor of the sample when reaching this reference point can be regarded as an antibody titer of antibody contained in the sample. For example, in the case of Method A, the dilution factor of the sample required for binding to all epitopes in the reaction system, i.e., the dilution factor at which the sample no longer shows any decrease in the bound amount of the monoclonal antibody of the present invention can be determined as an antibody titer of antibody contained in the sample. Likewise, in the case of Method B, the dilution factor of the sample required for binding inhibition of the monoclonal antibody of the present invention, i.e., the dilution factor at which the sample no longer shows any increase in the bound amount of the monoclonal antibody of the present invention can be determined as an antibody titer of antibody contained in the sample.

A higher dilution factor indicates a higher antibody titer, while a lower dilution factor indicates a lower antibody titer.

In Method A above, the term "contact" is intended to mean that the test sample or a mixture of the monoclonal antibody of the present invention and the test sample is placed together with the HPV antigen in an environment where they can be reacted under certain conditions, and more specifically intended to mean that antibodies in the test sample or the monoclonal antibody of the present invention is placed together with the HPV antigen in an environment where the antibodies or the monoclonal antibody bind to the HPV antigen under certain conditions. The term "contact" encompasses mixing of the test sample or the mixture with the HPV antigen, mixing of the HPV antigen with the test sample or the mixture, coexistence of an HPV antigen-immobilized solid support with the test sample or the mixture, injection of the test sample or the mixture into the solid support, etc. The antibody in the test sample or the monoclonal antibody of the present invention is bound to the HPV antigen upon contact between the test sample, or the monoclonal antibody or the mixture thereof and the HPV antigen.

(i) Preparation of Test Samples

A preferred test sample is human whole blood or serum, etc. Whole blood may optionally be centrifuged at high speed to remove insoluble substances before being prepared as a test sample for ELISA/RIA or as a test sample for Western blotting, as described below.

For use as a test sample for ELISA/RIA, for example, the collected serum may be used directly or diluted as appropriate with a buffer. For use as a test sample for Western blotting (electrophoresis), for example, the serum may be used directly or diluted as appropriate with a buffer. In the case of dot/slot blotting, a test sample may be prepared in the same manner as above.

(ii) Immobilization of HPV Antigens on Solid Phase

To specifically detect cross-neutralizing antibody in the test sample thus obtained, HPV antigens may be precipitated by immunoprecipitation, ligand binding-based techniques or the like and used for detection without being immobilized on the solid phase, or alternatively, HPV antigens may be immobilized on solid supports (solid phase) and then used for detection. For protein immobilization on the solid phase, membranes used in Western blotting, dot blotting or slot blotting include nitrocellulose membranes (e.g., products of BioRad Laboratories), nylon membranes (e.g., Hybond-ECL (Amersham Pharmacia)), cotton membranes (e.g., Blot Absorbent Filter (BioRad Laboratories)) or polyvinylidene difluoride (PVDF) membranes (e.g., products of BioRad Laboratories), etc.

The so-called blotting techniques used to transfer antigen proteins from the electrophoresed gel to a membrane include wet blotting (CURRENT PROTOCOLS IN IMMUNOLOGY volume 2 ed by J. E. Coligan, A. M. Kruisbeek, D. H. Margulies, E. M. Shevach, W. Strober), as well as semi-dry blotting (see CURRENT PROTOCOLS IN IMMUNOL- OGY volume 2 (supra)). Instruments for use in dot blotting or slot blotting are also commercially available (e.g., Bio-Dot (BioRad Laboratories)).

On the other hand, for detection or quantification based on ELISA/RIA, HPV antigens or dilutions thereof (e.g., those diluted with phosphate-buffered saline (hereinafter referred to as "PBS") containing 0.05% sodium azide) are dispensed into specifically designed 96-well plates (e.g., Immunoplate Maxisorp (Nunc)) and then allowed to stand overnight at 4° C. to room temperature or at 37° C. for 1 to 3 hours, whereby the HPV antigens are immobilized on the solid phase by being adsorbed on the bottom surface of the wells.

(4) Measurement of Antibody Titer of Cross-Neutralizing Antibody

Techniques used here for antibody titer measurement include various known techniques such as radioimmunoassay (hereinafter referred to as "RIA"), solid-phase enzyme immunoassay (hereinafter referred to as "ELISA"), fluorescent antibody techniques, passive haemagglutination and so on, with ELISA being more preferred in terms of detection sensitivity, rapidity, accuracy, possible automation of operations, etc.

For example, according to ELISA, antibody titer measurement in the present invention may be accomplished by procedures as described below. First, purified or partially purified HPV antigen is adsorbed on the solid phase surface such as 96-well plates for ELISA, and then contacted with cross-neutralizing antibody in serial dilutions of a test sample (e.g., human serum) for a period of time and under conditions sufficient to form antibody/antigen conjugates. After washing, murine monoclonal antibody according to the present invention is contacted as a primary antibody, and the monoclonal antibody of the present invention is bound to epitopes remaining unbound to the antibody. Further, an enzyme-labeled anti-mouse antibody is added as a secondary antibody and bound to the murine monoclonal antibody. After washing, a substrate for the enzyme is added, and changes in absorbance induced by color development based on substrate degradation are measured to thereby calculate the antibody titer.

In addition to the above procedures, a test sample may be mixed with murine monoclonal antibody according to the present invention serving as a primary antibody before being provided for measurement.

The absorbance data obtained for serial dilutions (e.g., two or more steps, preferably three or more steps of dilutions) of each test sample can be used to quantify the cross-neutralizing antibody titer of each serum by parallel line assay. For parallel line assay, standard solutions containing the monoclonal antibody of the present invention can be used (see. Example 3 (Test Method 3)).

The HPV antigen used in the method of the present invention may be the whole or a part of HPV L2 protein expressed in *E. coli* cells or cultured cells, a capsid composed of HPV L1 and L2 proteins, a pseudovirus, or a synthetic peptide having a part of the L2 protein sequence.

The monoclonal antibody used in the method of the present invention may be 13B, 24B, or a mixture of 13B and 24B. Alternatively, the monoclonal antibody used in the method of the present invention is a monoclonal antibody according to the present invention; preferably a monoclonal antibody recognizing a common epitope in the HPV L2 protein; more preferably a monoclonal antibody comprising the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3) or a monoclonal antibody comprising the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3); even more preferably a monoclonal antibody whose heavy chain variable region is the amino acid sequence shown in SEQ ID NO: 7 and whose light chain variable region is the amino acid sequence shown in SEQ ID NO: 8 or a monoclonal antibody whose heavy chain variable region is the amino acid sequence shown in SEQ ID NO: 9 and whose light chain variable region is the amino acid sequence shown in SEQ ID NO: 10; or still even more preferably a monoclonal antibody produced by hybridoma cell line FERM BP-11304 or FERM BP-11305.

As described above, the monoclonal antibody of the present invention can be used for detection or assay of cross-neutralizing antibody on the basis of its specificity.

(i) Detection

For use in detection, the monoclonal antibody of the present invention may be labeled directly or used as a primary antibody in cooperation with a labeled secondary antibody specifically recognizing the antibody (recognizing an antibody of the same animal origin as used to prepare the monoclonal antibody).

Preferred types of labels include, but are not limited to, enzymes (alkaline phosphatase or horseradish peroxidase) or biotin (provided that enzyme-labeled streptavidin is further bound to biotin on the secondary antibody). For techniques using a labeled secondary antibody (or labeled streptavidin), various products of pre-labeled antibody (or streptavidin) are commercially available. In the case of RIA, an antibody labeled with a radioisotope such as $I^{125}$ is used and the assay is accomplished by using a liquid scintillation counter or the like.

By detecting the activity of these enzyme labels, the amount (titer) of cross-neutralizing antibody is determined. In the case of alkaline phosphatase or horseradish peroxidase, substrates which cause color development or light emission by the catalytic action of these enzymes are commercially available. In the present invention, enzyme labeling with horseradish peroxidase (HRP) is preferred for use.

In the case of using color-developing substrates, they can be visually detected in Western blotting or dot/slot blotting. In ELISA, they are preferably quantified by measuring the absorbance for each well with a commercially available microplate reader (the measurement wavelength varies from substrate to substrate).

On the other hand, in the case of using light-emitting substrates, they can be detected in Western blotting or dot/slot blotting by autoradiography on an X-ray film or an imaging plate or by photography with an instant camera, and may also be quantified by densitometry or with a Molecular Imager Fx system (BioRad Laboratories), etc. In the case of using light-emitting substrates in ELISA, enzyme activity is measured with an emission microplate reader (e.g., a product of BioRad Laboratories).

(ii) Measurement Operations

1) Western Blotting, Dot Blotting or Slot Blotting

First, to avoid non-specific adsorption of monoclonal antibody molecules, a membrane is pre-soaked (blocked) for a given period of time in a buffer containing an inhibitor of such non-specific adsorption (e.g., skimmed milk, casein, bovine serum albumin, gelatin, polyvinylpyrrolidone). A blocking solution is composed of, for example, 5% skimmed milk and 0.05% to 0.1% Tween 20 in phosphate-buffered saline (PBS) or tris-buffered saline (TBS). Skimmed milk may be replaced with Block Ace (Dainippon Pharmaceutical Co., Ltd., Japan), 1% to 10% bovine serum albumin, 0.5% to 3% gelatin or 1% polyvinylpyrrolidone, etc. The blocking time is 16 to 24 hours at 4° C. or 1 to 3 hours at room temperature.

Next, the membrane is washed with PBS or TBS containing 0.05% to 0.1% Tween 20 (hereinafter also referred to as "washing solution") to remove excess blocking solution, and then soaked for a given period of time in a solution of a test sample or the monoclonal antibody of the present invention diluted as appropriate with the blocking solution, whereby cross-neutralizing antibody in the test sample or the monoclonal antibody is bound to antigen molecules on the membrane to form antibody/antigen conjugates. The dilution factor used for the sample or the monoclonal antibody may be determined by a preliminary western blotting experiment. This antibody reaction operation is preferably performed at room temperature for 2 hours. After completion of the antibody reaction operation, the membrane is washed with the washing solution. Then, to the antibody/antigen conjugates formed above, the monoclonal antibody or the test sample diluted as appropriate is added and bound. If the monoclonal antibody used is a labeled one, detection can be performed immediately. If an unlabeled monoclonal antibody is used, the conjugates are further subjected to secondary antibody reaction. In the case of using a commercially available product as a labeled secondary antibody, it is diluted 2000-fold to 20000-fold with the blocking solution before use (according to the attached instructions if a preferred dilution factor is found therein). After washing off the primary antibody, the membrane is soaked in a secondary antibody solution at room temperature for 45 minutes to 1 hour and washed with the washing solution, followed by detection in a manner suitable for the labeling method used. The washing operation may be accomplished, for example, as follows: the membrane is first shaken in the washing solution for 15 minutes, further shaken for 5 minutes after replacement of the washing solution with a fresh one, and then shaken again for 5 minutes after replacement of the washing solution with a fresh one. If necessary, the washing solution may further be replaced during the washing operation.

2) ELISA/RIA

First, to avoid non-specific adsorption of monoclonal antibody molecules onto the bottom surface of wells in an HPV antigen-immobilized plate, the plate is blocked before use, as in the case of Western blotting. Blocking conditions are as described above for Western blotting.

Next, the wells are washed with PBS or TBS containing 0.05% to 0.1% Tween 20 (hereinafter also referred to as "washing solution") to remove excess blocking solution, and a solution of a test sample diluted as appropriate with the washing solution is then dispensed into the wells, followed by incubation for a given period of time to allow cross-neutralizing antibody in the sample to bind to antigen molecules. The dilution factor used for the sample may be determined, for example, by a preliminary ELISA experiment. This antibody reaction operation is preferably performed at room temperature for about 1 hour. After completion of the antibody reaction operation, the wells are washed with the washing solution. Then, a solution of the monoclonal antibody of the present invention diluted as appropriate is dispensed into the wells and bound to the antigen molecules by being incubated for a given period of time. If the monoclonal antibody used is a labeled one, detection can be performed immediately. If an unlabeled monoclonal antibody is used, the plate is further subjected to secondary antibody reaction. In the case of using a commercially available product as a labeled secondary antibody, it is diluted 2000-fold to 20000-fold with the washing solution before use (according to the attached instructions if a preferred dilution factor is found therein). After washing off the primary antibody, a secondary antibody solution is dispensed into the wells and incubated at room temperature for 1 to 3 hours. The wells are washed with the washing solution, followed by detection in a manner suitable for the labeling method used. The washing operation may be accomplished, for example, as follows: the washing solution is first dispensed into the wells, and the plate is shaken for 5 minutes, further shaken for 5 minutes after replacement of the washing solution with a fresh one, and then shaken again for 5 minutes after replacement of the washing solution with a fresh one. If necessary, the washing solution may further be replaced during the washing operation.

It should be noted that the test sample and the monoclonal antibody of the present invention may be used in reverse order, as appropriate.

The present invention also provides a kit for determining the presence or the antibody titer of cross-neutralizing antibody against HPV in a test sample or a kit for measuring the antibody titer of cross-neutralizing antibody against HPV. More specifically, such a kit comprises (a) an HPV antigen immobilized on a solid support, (b) the monoclonal antibody of the present invention, and (c) a labeled secondary antibody recognizing the monoclonal antibody of the present invention. Such a kit may further comprise a reagent required for measurement, a buffer, water, a container, an instruction manual, etc.

(5) Pharmaceutical Preparations Comprising the Monoclonal Antibody of the Present Invention The monoclonal antibody of the present invention can be used as a pharmaceutical preparation such as a prophylactic or therapeutic agent for HPV, i.e., a prophylactic or therapeutic agent for HPV infection or HPV infection-induced diseases. For use as a pharmaceutical preparation, the monoclonal antibody should be compatible with humans or animal species in need of treatment or prevention of such a disease.

HPV infection-induced diseases include uterine cervical cancer, condyloma acuminatum, verruca, and other diseases. The prophylactic or therapeutic agent for HPV comprising the monoclonal antibody of the present invention is preferably a prophylactic or therapeutic agent for uterine cervical cancer.

In one preferred embodiment, the monoclonal antibody of the present invention for use as a pharmaceutical preparation has a reduced risk of antigenicity when administered to humans More specifically, it is a complete human antibody, a humanized antibody or a chimeric antibody such as a mouse-human chimeric antibody, and particularly preferably a complete human antibody. Humanized and chimeric antibodies may be prepared in a genetic engineering manner according to the procedures described later. Complete human antibodies may be produced by human-human (or mouse) hybridomas, but they are desirably produced by human antibody-producing animals (e.g., mice) or phage display techniques as described later in order to provide large amounts of antibodies in a stable manner and at low cost.

(i) Preparation of Chimeric Antibody

As used herein, the term "chimeric antibody" is intended to mean an antibody in which the sequences of H chain and L chain variable regions ($V_H$ and $V_L$) are derived from one mammalian species, while the sequences of constant regions ($C_H$ and $C_L$) are derived from another mammalian species. The sequences of the variable regions are preferably derived from an animal species (e.g., mice) from which hybridomas can be easily prepared, whereas the sequences of the constant regions are preferably derived from a mammalian species which is a target to be administered.

Techniques for chimeric antibody preparation include, for example, the method described in U.S. Pat. No. 6,331,415 or partially modified methods therefrom. More specifically, mRNA or total RNA is first prepared in a routine manner from hybridomas (e.g., mouse-mouse hybridomas) producing the monoclonal antibody of the present invention obtained as described above, and then used to synthesize cDNA. Using the cDNA as a template, PCR is performed in a routine manner with appropriate primers (e.g., oligo DNA comprising a nucleotide sequence encoding the N-terminal sequence of $V_H$ or $V_L$ as a sense primer, and oligo DNA hybridizable with a nucleotide sequence encoding the N-terminal sequence of $C_H$ or $C_L$ as an antisense primer (see, e.g., Bio/Technology, 9: 88-89, 1991)) to thereby amplify and purify DNAs encoding $V_H$ and $V_L$. In the same manner, RNA prepared from another mammalian (e.g., human) lymphocytes or the like is used as a template in RT-PCR to amplify and purify DNAs encoding $C_H$ and $C_L$. $V_H$ and $V_L$ are ligated to $C_H$ and $C_L$, respectively, in a routine manner, and the resulting chimeric H chain DNA and chimeric L chain DNA are each inserted into an appropriate expression vector (e.g., a vector comprising a promoter (e.g., CMV promoter, SV40 promoter) having transcriptional activity in CHO cells, COS cells, mouse myeloma cells, etc.). The DNAs encoding these two chains may be inserted into separate vectors or may be inserted in tandem into a single vector. The resulting chimeric H chain and chimeric L chain expression vectors are used to transform host cells. Examples of host cells include animal cells, such as mouse myeloma cells as mentioned above, as well as Chinese hamster ovary (CHO) cells, monkey-derived COS-7 and Vero cells, rat-derived GHS cells, etc. Transformation may be accomplished in any manner applicable to animal cells, preferably by electroporation or the like. After culture in a medium suitable for the host cells for a given period of time, the culture supernatant is collected and purified in the same manner as described above to isolate chimeric monoclonal antibody molecules. Alternatively, when germ line cells of animals (e.g., cows, goats, chickens), for which transgenic techniques have been established and know-how of large-scale breeding as domestic animals (domestic fowls) has been accumulated, are used as host cells to create transgenic animals in a routine manner, chimeric monoclonal antibody can be obtained with ease and in large amounts from milk or eggs of the resulting animals. Further, plant cells (e.g., maize, rice, wheat, soybean or tobacco cells), for which transgenic techniques have been established and which have been cultivated as major crops on a large scale, are used as host cells to create transgenic plants, e.g., by microinjection or electroporation into protoplasts or by particle gun or Ti vector transformation of intact cells, whereby chimeric monoclonal antibody can be obtained in large amounts from the resulting seeds or leaves.

The resulting chimeric monoclonal antibody is digested with papain to give Fab and with pepsin to give $F(ab')_2$.

Alternatively, DNAs encoding mouse $V_H$ and $V_L$ may be ligated via an appropriate linker, for example, DNA encoding a peptide composed of 1 to 40 amino acids, preferably 3 to 30 amino acids, more preferably 5 to 20 amino acids (e.g., $[Ser-(Gly)_m]_n$ or $[(Gly)_m-Ser]_n$ (wherein m is an integer of 0 to 10, and n is an integer of 1 to 5)) to give scFv. Moreover, DNA encoding $C_{H3}$ may further be ligated via an appropriate linker to give a minibody monomer, or alternatively, DNA encoding full-length $C_H$ may further be ligated via an appropriate linker to give scFv-Fc. DNAs encoding such antibody molecules modified (conjugated) in a genetic engineering manner can be expressed in microorganisms (e.g., E. coli, yeast) when placed under the control of an appropriate promoter, thereby allowing large-scale production of antibody molecules.

When DNAs encoding mouse $V_H$ and $V_L$ are inserted in tandem downstream of a single promoter and then introduced into E. coli cells, a dimer called Fv is formed by monocistronic gene expression. Likewise, when appropriate amino acids in the framework regions (FRs) of $V_H$ and $V_L$ are each replaced with Cys by molecular modeling, a dimer called dsFv is formed by intermolecular disulfide linking between these two chains.

(ii) Humanized Antibody

As used herein, the term "humanized antibody" is intended to mean an antibody in which the sequences of all regions but complementarity determining regions (CDRs) present in the variable regions (i.e., constant regions and FRs in the variable regions) are of human origin, while only the CDR sequences are derived from another mammalian species. Preferred other mammalian species include, for example, animal species (e.g., mice) from which hybridomas can be easily prepared. The term "complete human antibody" is intended to mean an antibody in which all the sequences of both light and heavy chains including CDRs are essentially derived from human genes.

Techniques for humanized antibody preparation include, for example, the methods described in U.S. Pat. Nos. 5,225,539, 5,585,089, 5,693,761 and 5,693,762 or partially modified methods therefrom. More specifically, as in the case of chimeric antibody described above, DNAs encoding $V_H$ and $V_L$ derived from a non-human mammalian species (e.g., mouse) are isolated and then sequenced in a routine manner with an automatic DNA sequencer (e.g., a product of Applied Biosystems). The resulting nucleotide sequences or amino acid sequences deduced therefrom are analyzed against a known antibody sequence database [e.g., Kabat database (see Kabat et al., "Sequences of Proteins of Immunological Interest", US Department of Health and Human Services, Public Health Service, edited by NIH, 5th edition, 1991)] to determine CDRs and FRs in both chains. Nucleotide sequences are designed such that CDR coding regions in nucleotide sequences encoding the L chain and H chain of human antibody whose FR sequences are similar to the determined FR sequences [e.g., human κ (type L chain subgroup I and human H chain subgroup II or III (see Kabat et al., 1991 (supra))] are replaced with nucleotide sequences encoding the determined heterologous CDRs. These nucleotide sequences are divided into fragments of approximately 20 to 40 bases, and sequences complementary to these nucleotide sequences are also divided into fragments of approximately 20 to 40 bases such that they alternately overlap with the above fragments. The fragments are each synthesized with a DNA synthesizer, and they may be hybridized and ligated in a routine manner to construct DNAs encoding $V_H$ and $V_L$ having FRs of human origin and CDRs derived from another mammalian species. For more rapid and efficient grafting of CDRs derived from another mammalian species into $V_H$ and $V_L$ of human origin, PCR-based site-specific mutagenesis is preferred for this purpose. Examples of such a technique include sequential CDR grafting described in JP 5-227970 A, etc. The thus obtained DNAs encoding $V_H$ and $V_L$ may be ligated to DNAs encoding $C_H$ and $C_L$ of human origin, respectively, in the same manner as described above for chimeric antibody and then introduced into appropriate host cells to thereby obtain humanized antibody-producing cells or transgenic animals/plants.

As in the case of chimeric antibody, humanized antibody can also be converted by genetic engineering procedures into scFv, scFv-Fc, minibody, dsFv, Fv and so on, and can be produced in microorganisms (e.g., E. coli, yeast) when using an appropriate promoter.

Techniques for humanized antibody preparation can also be adapted, for example, to prepare monoclonal antibody which can be preferably administered to other animal species, for which hybridoma preparation techniques have not yet been established, as exemplified by animals widely bred as domestic animals (domestic fowls) including cows, pigs, sheep, goats and chickens, as well as pet animals including dogs and cats.

(iii) Preparation of Complete Human Antibody Using Human Antibody-Producing Animals Into non-human warm-blooded animals whose endogenous immunoglobulin (Ig) genes are knocked out (KO), functional human Ig genes are introduced. Upon immunization with an antigen, the animals will produce human antibodies instead of their own antibodies. Thus, when using animals (e.g., mice) for which hybridoma preparation techniques have been established, it will be possible to obtain complete human monoclonal antibody in the same manner as conventionally used for preparation of mouse monoclonal antibody. First, a mouse transformed with mini-genes for human Ig H and L chains by using standard transgenic (Tg) techniques is crossed with a mouse whose endogenous mouse Ig genes are inactivated by using standard KO techniques to obtain human antibody-producing mice (see Immunol. Today, 17: 391-397, 1996). Some of the human monoclonal antibodies produced by these mice are already under clinical trials, and no report has been made for the production of anti-human Ig human antibody (HAHA).

Thereafter, Abgenix Inc. [trade name: XenoMouuse (see, e.g., Nat. Genet., 15: 146-156, 1997; U.S. Pat. No. 5,939,598)] and Medarex Inc. [trade name: Hu-Mab Mouse (see, e.g., Nat. Biotechnol., 14: 845-851, 1996; U.S. Pat. No. 5,545,806)] created Tg mice carrying larger human Ig genes by using a yeast artificial chromosome (YAC) vector. Such mice allowed production of human antibody with a wider repertoire. However, human Ig genes achieve their diversity because antigen-binding sites are encoded, e.g., by VDJ exons (for H chain) constructed from various combinations of about 80 types of V fragments, about 30 types of D fragments and 6 types of J fragments. For this reason, the full length reaches about 1.5 Mb for H chain (chromosome 14), about 2 Mb for κL chain (chromosome 2) and about 1 Mb for λL chain (chromosome 22). In order that the same wide diversity of antibody repertoire as in humans is reproduced in other animal species, it is desirable to introduce the full-length sequence of each Ig gene. However, DNAs insertable into conventional gene transfer vectors (e.g., plasmid, cosmid, BAC, YAC) are usually several kb to several hundreds of kb in length, and it is therefore difficult to introduce full-length sequences by conventional techniques for transgenic animal preparation which involve injecting cloned DNAs into fertilized eggs.

Tomizuka et al. (Nat. Genet., 16: 133-143, 1997) introduced native human chromosome fragments (hCF) carrying Ig genes into mice (trans-chromosomic (TC) mice) to create mice having the full-length human Ig genes. Namely, first, human-mouse hybrid cells having human chromosomes, in which chromosome 14 including the H chain gene and chromosome 2 including the κL chain gene are each labeled, e.g., with a drug-resistant marker, are treated for about 48 hours with a spindle formation inhibitor (e.g., colcemid) to prepare microcells containing one to several chromosomes or fragments thereof encapsulated within the nuclear membrane, followed by micronuclear fusion to introduce the chromosomes into mouse ES cells. Hybrid ES cells carrying the chromosomes or fragments thereof having the human Ig genes are selected with a drug-containing medium and microinjected into mouse embryos in the same manner as commonly used for KO mouse preparation. The resulting chimeric mice are analyzed for their coat color pattern or the like to select germ line chimeras, thereby establishing a TC mouse strain carrying the human chromosome 14 fragment (TC(hCF14)) and a TC mouse strain carrying the human chromosome 2 fragment (TC(hCF2)). Mice whose endogenous H chain and κL chain genes are knocked out (KO (IgH) and KO(IgK), respectively) are created in a routine manner, and these four strains are repeatedly crossed to establish a mouse strain having all of the four types of gene mutations (double TC/KO).

When double TC/KO mice as created above are treated in the same manner as commonly used for preparation of mouse monoclonal antibody, antigen-specific human monoclonal antibody-producing hybridomas can be prepared. However, such mice are disadvantageous in that hybridomas are obtained less efficiently than in normal mice because hCF2 including the κL chain gene is unstable in mouse cells.

On the other hand, the above Hu-Mab mice comprise about 50% of the κL chain gene, but have a structure in which variable region clusters are doubled. Thus, they show the same K chain diversity as observed in mice with the full-length gene (on the other hand, Hu-Mab mice show a low H chain diversity and insufficient responses to antigen because they comprise only about 10% of the H chain gene). Moreover, the κL chain gene is stably maintained in cells of these mice because it is inserted into mouse chromosomes through a YAC vector (Igκ-YAC). Based on these advantages, TC(hCF14) and Hu-Mab mice are crossed to create a mouse stably carrying hCF14 and Igκ-YAC (trade name: KM mouse), which achieves the same efficiency of hybridoma production and the same antibody's affinity to antigen as in normal mice.

Furthermore, for more complete reproduction of the same diverse antibody repertoire as in humans, it is possible to create human antibody-producing animals further modified to have the λL chain gene. Such animals may be obtained in the same manner as described above by creating a TC mouse modified to have human chromosome 22 or fragments thereof carrying the λL chain gene (TC(hCF22)) and then crossing this mouse with the above double TC/KO mouse or KM mouse, or alternatively, may be obtained by constructing a human artificial chromosome (HAC) including, for example, the H chain and XL chain gene loci and then introducing the HAC into mouse cells (Nat. Biotechnol., 18: 1086-1090, 2000).

(iv) Preparation of Complete Human Antibody Using Phage Display Human Antibody Library Another approach for preparation of complete human antibody is based on phage display technology. In this approach, PCR-induced mutations may sometimes be introduced into regions other than CDRs, and hence there are a few reports of HAHA production in clinical trials. On the other hand, this approach is advantageous in that there is no risk of cross-species viral infection arising from host animals and that the antibody's specificity is not limited (antibodies against forbidden clones, sugar chains or the like can also be easily prepared), etc.

Techniques for preparation of a phage display human antibody library include, but are not limited to, the following.

Although any phage may be used, filamentous phage (Ff bacteriophage) is generally preferred for use. To display a foreign protein on the phage surface, for example, the foreign protein is expressed and displayed by being fused with any of coat proteins g3p and g6p to g9p, frequently fused with the N-terminal end of g3p or g8p. Examples of a phage display vector include: 1) those for introduction of a foreign gene in a state fused to the coat protein genes in the phage genome to thereby display all the coat proteins as fusion proteins with the foreign protein on the phage surface, as well as 2) those for insertion of a gene encoding a fusion protein separately from the wild-type coat protein genes to thereby express the fusion protein and the wild-type coat proteins at the same time, and 3) those designed such that $E.$ $coli$ cells having a phagemid vector carrying a gene encoding a fusion protein are infected with a helper phage having the wild-type coat protein genes to produce phage particles which express the fusion protein and the wild-type coat proteins at the same time. However, phage display vectors of type 2) or 3) are used for antibody library preparation because phage display vectors of type 1) lose their infection ability when a large foreign protein is fused.

As examples of specific vectors, those described in Holt et al. (Curr. Opin. Biotechnol., 11: 445-449, 2000) can be presented. For example, pCES1 (see J. Biol. Chem., 274: 18218-18230, 1999) is an Fab-expressing phagemid vector that comprises, under the control of a single lactose promoter, DNA encoding the κL chain constant region downstream of the g3p signal peptide and DNA encoding $C_{H3}$ downstream of the g3p signal peptide, a His-tag, a c-myc tag, an amber stop codon (TAG), followed by the g3p coding sequence. This vector displays Fab on the g3p coat protein when introduced into $E.$ $coli$ cells having an amber mutation, whereas soluble Fab antibody is produced upon expression in HB2151 or other strains having no amber mutation. As an scFv-expressing phagemid vector, pHEN1 (J. Mol. Biol., 222:581-597, 1991) or the like is used, by way of example.

On the other hand, examples of a helper phage include M13-KO7, VCSM13 and so on.

Other examples of phage display vectors include those designed such that a sequence including a cysteine-encoding codon is ligated to each of the 3'-terminal end of the antibody gene and the 5'-terminal end of the coat protein gene to express these two genes independently (not as a fusion protein) at the same time, whereby the antibody can be displayed on the coat protein on the phage surface via S—S bonding between the introduced cysteine residues (CysDisplay™ technique, Morphosys).

A human antibody library may be of any type, including a naive/non-immunized library, a synthetic library, an immunized library, etc.

A naive/non-immunized library is a library obtained as follows: $V_H$ and $V_L$ genes possessed by normal humans are obtained by RT-PCR and then randomly cloned into phage display vectors as mentioned above. In general, mRNAs derived from lymphocytes in peripheral blood, bone marrow, tonsil or the like from normal humans are used as templates. To avoid V gene biases such as clinical history, only mRNAs derived from IgM where no class switch is induced by antigen sensitization are amplified, and the library thus prepared is particularly called a naive library. Typical examples include libraries of CAT Inc. (see J. Mol. Biol., 222: 581-597, 1991; Nat. Biotechnol., 14: 309-314, 1996), libraries of MRC Inc. (see Annu. Rev. Immunol., 12: 433-455, 1994), libraries of Dyax Inc. (see J. Biol. Chem., 1999 (supra); Proc. Natl. Acad. Sci. USA, 14: 7969-7974, 2000), etc.

A synthetic library is obtained as follows: functional specific antibody genes in human B cells are selected and antigen-binding regions (e.g., CDR3) in their V gene fragments are replaced with DNAs encoding random amino acid sequences in appropriate size to construct a library. Such a synthetic library is regarded as excellent in antibody expression efficiency and stability because the library can be constructed with combinations of $V_H$ and $V_L$ genes which produce functional scFv and Fab, since the beginning. Typical examples include HuCAL libraries of Morphosys Inc. (see J. Mol. Biol., 296: 57-86, 2000), libraries of BioInvent Inc. (see Nat. Biotechnol., 18: 852, 2000), libraries of Crucell Inc. (see Proc. Natl. Acad. Sci. USA, 92: 3938, 1995; J. Immunol. Methods, 272: 219-233, 2003), etc.

An immunized library is obtained as follows: in the same manner as described above for the naive/non-immunized library, mRNAs are prepared from lymphocytes taken from humans with increased antibody titers against target antigens in blood (e.g., patients with cancers, autoimmune diseases, infections or the like and subjects receiving vaccination) or from human lymphocytes artificially immunized with target antigens by in vitro immunization as described above, and $V_H$ and $V_L$ genes are amplified by RT-PCR techniques to construct a library. It is possible to obtain a desired antibody from a library of relatively small size because desired antibody genes are contained in the library at the beginning.

Although a wider diversity of library is more preferred, about $10^8$ to $10^{11}$ clones are suitable for practical use in light of the number of phages which can be handled in the following panning operation ($10^{11}$ to $10^{13}$ phages) and the number of phages required to isolate and amplify clones in ordinary panning (100 to 1,000 phages/clone). A library of about $10^8$ clones usually allows screening of antibody having a Kd value on the order of $10^{-9}$.

The process of selecting an antibody against a target antigen by phage display techniques is called panning More specifically, for example, an antigen-immobilized carrier and a phage library are contacted with each other, unbound phages are washed off, and the bound phages are then released from the carrier and infected into $E.$ $coli$ cells to proliferate the phages. Such a series of operations are repeated about 3 to 5 times to enrich phages displaying an antigen-specific antibody. Examples of a carrier used for antigen immobilization include various carriers commonly used in antigen-antibody reaction or affinity chromatography, such as insoluble polysaccharides (e.g., agarose, dextran, cellulose), synthetic resins (e.g., polystyrene, polyacrylamide, silicone), microplates, tubes, membranes, columns and beads which are made of glass, metal or the like, as well as sensor chips for surface plasmon resonance (SPR), etc. Antigen immobilization may be accomplished by physical adsorption or by chemical bonding commonly used to insolubilize or immobilize proteins or enzymes, etc. For example, the biotin-(strept)avidin system or the like is preferred for use. If the endogenous ligand serving as a target antigen is a small molecule such as a peptide, special attention should be given to prevent the region used as an antigenic determinant from being masked by conjugation with the carrier. For washing of unbound phages, a blocking solution such as a BSA solution (once or twice) and PBS containing a surfactant (e.g., Tween) (3 to 5 times) may be used sequentially. There is also a report showing that the use of citrate buffer (pH 5) or the like is preferred. For release of specific phages, an acid (e.g., 0.1 M hydrochloric acid) is generally used, although it is possible to release the phages by cleavage with a specific protease (for example, a gene sequence encoding a trypsin cleavage site can be introduced into the joint between antibody gene and coat protein gene. In this case, since wild-type coat proteins are displayed on the surface of phages released, the phages can be infected into and proliferate in E. coli cells even when the coat proteins are all expressed as fusion proteins), competitive release with a soluble antigen, or reduction of S—S bonds (for example, in CysDisplay™ described above, an appropriate reducing agent is used after panning to dissociate antibody molecules from coat proteins, whereby antigen-specific phages can be collected). When released with an acid, the released phages are neutralized with Tris or the like and then infected into E. coli cells. After culture, the phages are collected in a routine manner.

Once phages displaying an antigen-specific antibody have been enriched by panning, these phages are infected into E. coli cells and then seeded on plates for cloning. The phages are collected again and confirmed for their antigen-binding activity by the above techniques for antibody titer measurement (e.g., ELISA, RIA, FIA) or by techniques based on FACS or SPR.

To isolate and purify antibody molecules from the selected phage clones displaying an antigen-specific antibody, for example, if the phage display vector used is a vector carrying an amber stop codon introduced into the joint between antibody gene and coat protein gene, soluble antibody molecules are produced and secreted into the periplasm or medium when the phages are infected into E. coli (e.g., strain HB2151) having no amber mutation, so that the cell wall is lysed with lysozyme to collect the extracellular fraction, which is then purified in the same manner as described above. When the vector has been modified to carry a His-tag or a c-myc tag, antibody molecules can be easily purified with an IMAC or anti-c-myc antibody column, etc. Alternatively, if cleavage with a specific protease is used in panning, antibody molecules are separated from the phage surface upon treatment with this protease, so that desired antibody molecules can be purified by performing the same purification operations.

Techniques for complete human antibody preparation using a human antibody-producing animal and a phage display human antibody library can also be adapted to prepare monoclonal antibodies of other animal species, as exemplified by animals widely bred as domestic animals (domestic fowls) including cows, pigs, sheep, goats and chickens, as well as pet animals including dogs and cats. In non-human animals, the use of an immunized library is more effective because there are fewer ethical problems about artificial immunization with target antigens.

A prophylactic and/or therapeutic agent comprising the monoclonal antibody of the present invention has low toxicity and may be administered directly as a solution or as a pharmaceutical composition in any suitable dosage form to humans or mammals (e.g., rats, rabbits, sheep, pigs, cows, cats, dogs, monkeys) by the parenteral or oral route.

The monoclonal antibody of the present invention may be administered either alone or as a suitable pharmaceutical composition. Such a pharmaceutical composition used for administration may comprise the monoclonal antibody of the present invention or a salt thereof and a pharmacologically acceptable carrier, diluent or excipient. Such a pharmaceutical composition is provided in any dosage form suitable for oral or parenteral administration.

For parenteral administration, for example, compositions such as injections and suppositories are used, and injections may encompass dosage forms such as intravenous injections, subcutaneous injections, intracutaneous injections, intramuscular injections, drip infusions, etc.

Such injections may be prepared in a known manner. For preparation of injections, for example, the above monoclonal antibody of the present invention or a salt thereof may be dissolved, suspended or emulsified in a sterile aqueous or oil-based solution commonly used for injections. Examples of an injectable aqueous solution used for this purpose include physiological saline, an isotonic solution containing glucose and other auxiliary agents, and so on, which may be used in combination with an appropriate solubilizer such as an alcohol (e.g., ethanol), a polyalcohol (e.g., propylene glycol, polyethylene glycol), a nonionic surfactant (e.g., Polysorbate 80, HCO-50 (polyoxyethylene (50 mol) adduct of hydrogenated castor oil)), etc. Examples of an oil-based solution used for this purpose include sesame oil, soybean oil and so on, which may be used in combination with a solubilizer such as benzyl benzoate, benzyl alcohol, etc. The prepared injectable solutions are preferably filled into appropriate ampules. Suppositories for intrarectal administration may be prepared by mixing the above monoclonal antibody or a salt thereof with a base commonly used for suppositories.

Compositions for oral administration include solid or liquid dosage forms, more specifically tablets (including sugar-coated tablets and film-coated tablets), pills, granules, powders, capsules (including soft capsules), syrups, emulsions, suspensions and so on. Such compositions may be prepared in a known manner and may comprise carriers, diluents or excipients commonly used in the field of formulations. Examples of carriers and excipients used for tablets include lactose, starch, sucrose, and magnesium stearate.

These parenteral or oral pharmaceutical compositions are advantageously formulated into unit dosage forms suited to the dose of the active ingredient. Examples of such unit dosage forms include tablets, pills, capsules, injections (ampules), and suppositories. The content of the monoclonal antibody is usually about 5 to 500 mg per unit dosage form. In particular, the above monoclonal antibody is preferably contained in an amount of about 5 to 100 mg for injections and about 10 to 250 mg for other dosage forms.

It should be noted that each composition described above may comprise other active ingredients as long as they do not cause unwanted interactions when combined with the above monoclonal antibody.

The dose of the prophylactic, therapeutic or diagnostic agent (pharmaceutical preparation) containing the monoclonal antibody of the present invention will vary depending on the target to be administered, the disease to be treated or diagnosed, symptoms, the route of administration, etc. For example, when used for treatment of uterine cervical cancer in adults, the monoclonal antibody of the present invention is advantageously administered at a single dose of generally about 0.01 to 20 mg/kg body weight, preferably about 0.1 to 10 mg/kg body weight, more preferably about 0.1 to 5 mg/kg body weight, about once to five times a day, preferably about once to three times a day, by the intravenous route. For other cases of parenteral administration (e.g., subcutaneous administration) and oral administration, corresponding doses may be administered. If the symptoms are particularly severe, the dose may be increased depending on the symptoms.

The pharmaceutical preparation of the present invention may be provided in the form of a kit. Such a kit may comprise the pharmaceutical preparation of the present invention, as well as an additional active ingredient, an additional pharmaceutical preparation, an instruction manual, a container, etc.

(6) Diagnostic Reagent for HPV Infection Comprising the Monoclonal Antibody of the Present Invention The monoclonal antibody of the present invention may be used as a diagnostic reagent for HPV infection. To detect HPV infection using the monoclonal antibody of the present invention, for example, proteins in a sample (e.g., a cervical scraped cell sample) are first immobilized on the bottom surface of wells in a multi-well plate (e.g., a 96-well or 384-well plate) or on a membrane and then provided for detection of HPV in the sample using the monoclonal antibody of the present invention. Among these techniques, those using a multi-well plate (e.g., a 96-well or 384-well plate) are generally called solid-phase enzyme immunoassay (ELISA) or radioimmunoassay (RIA). On the other hand, techniques based on immobilization on a membrane include those in which proteins in a sample are transferred to a membrane after polyacrylamide electrophoresis (Western blotting) or those in which a sample or a dilution thereof is directly immersed into a membrane, i.e., so-called dot blotting or slot blotting.

EXAMPLES

The present invention will be further described in more detail by way of the following examples, which are provided for illustrative purposes only to describe detailed embodiments of the present invention and are not intended in any sense to limit the scope and meaning of the present invention or the illustrated embodiments thereof. Likewise, the scope of the present invention is not limited by the specific embodiments described herein. In addition to the descriptions in the specification, various modifications to the present invention will become apparent to those skilled in the art from the specification, claims and drawings.

All reference documents cited herein, including patents, patent applications and journal articles, are incorporated herein by reference in their entirety.

1. Preparation of Monoclonal Antibody Recognizing Human Papillomavirus Type 16 (HPV16) L2 Protein An artificially synthesized peptide (amino acids 56-75 of HPV16 L2 protein: P56/75 [SEQ ID NO: 1]) was conjugated with keyhole limpet hemocyanin (KLH) via cysteine to prepare an antigen (KLH-P56/75). This antigen (50 μg/animal) was intracutaneously inoculated into three Balb/c mice together with Freund's complete adjuvant (FCA). After 2, 4 and 6 weeks, the mice were boosted in the same manner. At 7 weeks after the first immunization, KLH-P56/75 (25 μg/animal) was intravenously injected together with FCA. At 6 days after the last immunization, spleen cells were collected from the mice and mixed with P3U1 myeloma cells at a ratio of 6:1, followed by cell fusion using 50% polyethylene glycol (PEG). The fused cells were selected in a medium supplemented with hypoxanthine, aminopterin and thymidine (HAT medium), and the cells were cloned. Cell clones secreting anti-HPV16 L2 antibody were screened by ELISA using HPV16 L1/L2-capsid as an antigen. As a result, two cell clones producing monoclonal antibodies 13B and 24B, respectively, were obtained. The cell producing antibody 13B and the cell producing 24B are referred to as "Mouse-Mouse hybridoma 13B" and "Mouse-Mouse hybridoma 24B," respectively, which were internationally deposited under the Budapest Treaty on Oct. 15, 2010 by the applicant of this application with the International Patent Organism Depositary, the National Institute of Advanced Industrial Science and Technology (Central 6, 1-1-1 Higashi, Tsukuba, Ibaraki, Japan (zip code: 305-8566)) and have international accession Nos. FERM BP-11304 and FERM BP-11305, respectively, each of which hybridoma cell line is available to the public via the International Patent Organism Depositary, the National Institute of Technology and Evaluation. These 13B- and 24B-producing cells were each intraperitoneally inoculated into five Balb/c mice to prepare mouse ascites samples enriched for the respective monoclonal antibodies.

2. Epitope Mapping of Monoclonal Antibodies 13B and 24B

Mutant peptides of P56/75 comprising deletions of several amino acids from the N- or C-terminal end or alanine substitutions for several amino acids were used as antigens (conjugated with KLH) in ELISA to determine amino acids essential for binding of each monoclonal antibody (double underlined in FIG. 2) and amino acids relevant to binding of each monoclonal antibody (underlined in FIG. 2) by analysis of their binding to the mutant peptides of P56/75 whose amino acids were partially replaced with alanines, thereby predicting the epitopes for monoclonal antibodies 13B and 24B. The antigen peptides used and the results of ELISA are shown in FIG. 1. These results indicated that 13B and 24B recognized regions covering amino acids 67-72 and 56-58 of the HPV16 L2 protein, respectively.

The thus predicted epitopes in P56/75 for monoclonal antibodies 13B and 24B are shown in FIG. 2, along with amino acid sequence regions conserved among high-risk types of HPV.

Figure 8:
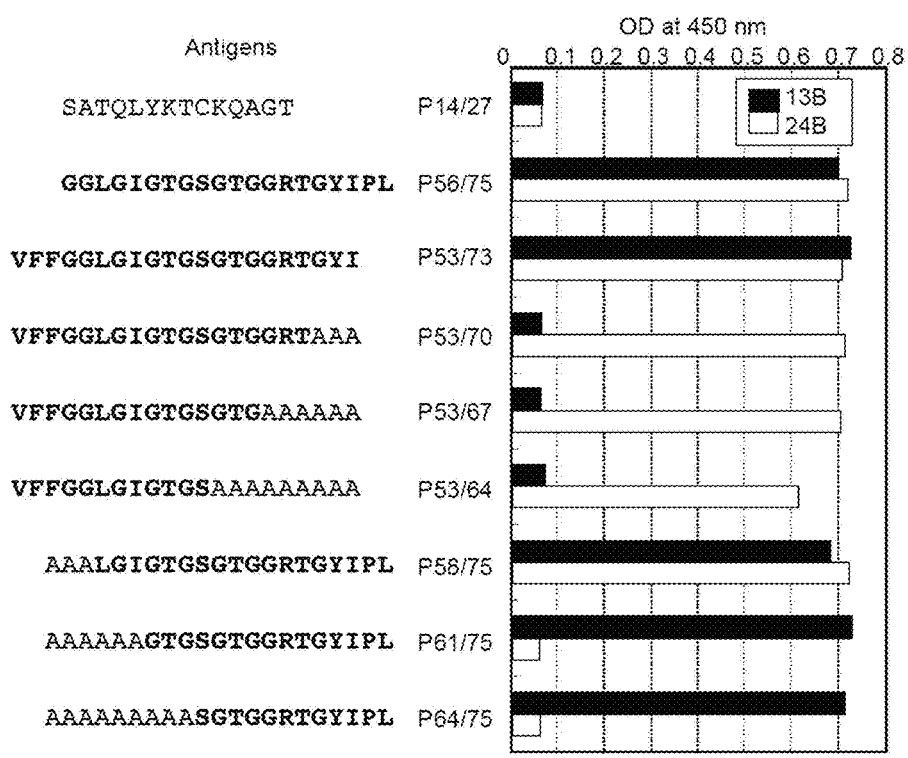
FIG. 8 shows the results of epitope mapping by ELISA (SEQ ID NOs: 26, 1, and 27 to 33).

Likewise, other mutant peptides of P56/75 comprising deletions several amino acids from the N- or C-terminal of or alanine substitutions for several amino acids end were used as antigens (conjugated with BSA) to determine the epitope for each monoclonal antibody in the same manner as described above. The antigen peptides used and the results of ELISA are shown in FIG. 8.

As a result of discussion, it is considered that the epitope recognized by 13B is located in the region of amino acids 64-73 in the HPV16 L2 protein, while the epitope recognized by 24B is located in the region of amino acids 58-67 in the HPV16 L2 protein (underlined in FIG. 9).

FIG. 9 shows the thus predicted epitopes in P56/75 for monoclonal antibodies 13B and 24B, along with amino acid sequence regions conserved among high-risk types of HPV.

3. Methods for Measuring Cross-Neutralizing Antibody Titers

Antibodies 13B and 24B were analyzed for their cross-inhibition capacity against infection of HPV pseudoviruses and for their cross-binding capacity toward HPV L1/L2-capsids. Cross-neutralizing antibody titers in test sera were deduced from measuring their ability to interfere with binding of antibody 13B or 24B to the HPV16 L2 antigen.

(Test Method 1) Measurement of Neutralizing Activity of Monoclonal Antibodies Against HPV16, 18, 31, 33, 35, 51, 52 and 58 Pseudoviruses (PsV)

(1) HPV16 or HPV58 L1 and L2 expression plasmids and a secretory alkaline phosphatase (SEAP) expression plasmid were mixed and transfected into 293FT cells. At 2 days after transfection, the cells were suspended in Detergent Buffer (0.35% Brij58, 1 μl RNase (Ambion #2286) in D-PBS (0.9 mM $CaCl_2$, 10 mM $MgCl_2$)) and incubated overnight at 37° C. After being allowed to stand on ice for 5 minutes, the cells were centrifuged at 10,000 g at 4° C. for 10 minutes to collect the supernatant. The collected supernatant was overlaid on 27%, 33%, 39% iodixanol (prepared with 0.8 M NaCl in PBS) and ultracentrifuged at 50,000 rpm at 16° C. for 3.5 hours. After ultracentrifugation, a fraction containing HPV16 or HPV58 pseudovirus (PsV) was collected and provided for neutralization experiments.

Figure 3:
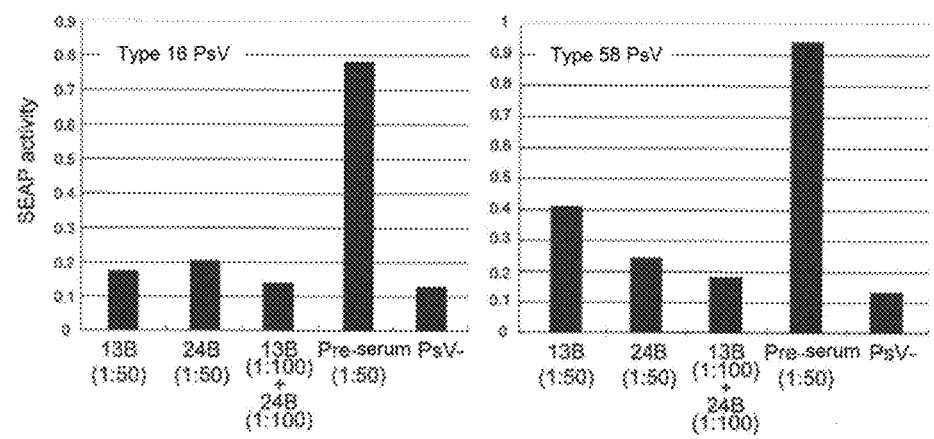
FIG. 3 shows neutralization of type 16 and 58 pseudoviruses by monoclonal antibodies 13B and 24B.
Figure 4:
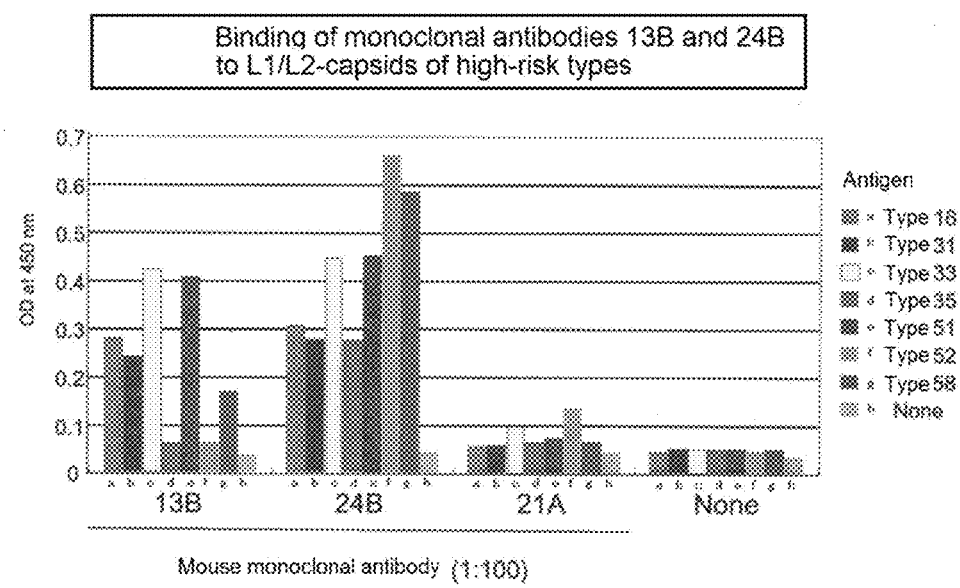
FIG. 4 shows binding of monoclonal antibodies 13B and 24B to L1/L2-capsids of high-risk types.
Figure 10:
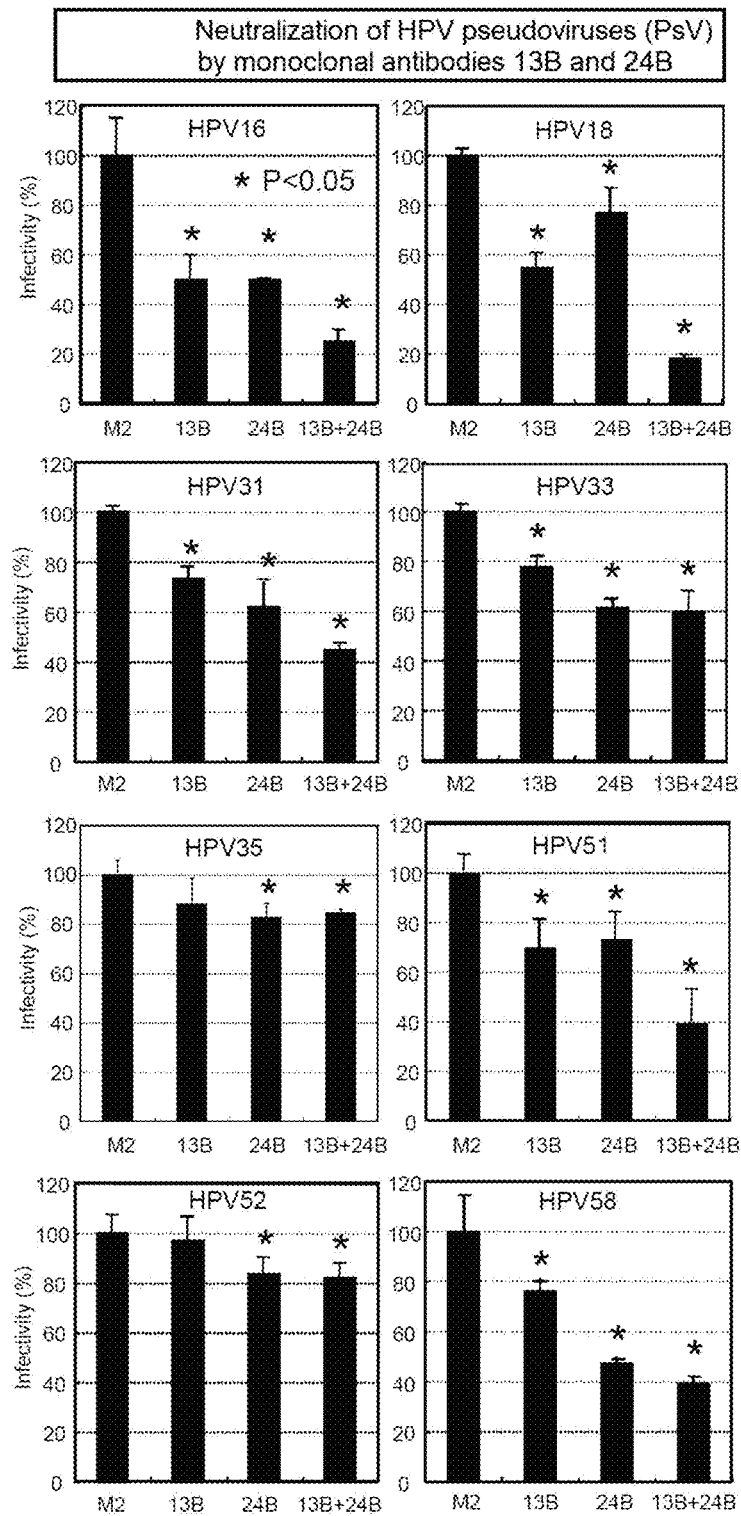
FIG. 10 shows neutralization of type 16, 18, 31, 33, 35, 51, 52 and 58 pseudoviruses by monoclonal antibodies 13B and 24B.
Figure 11:
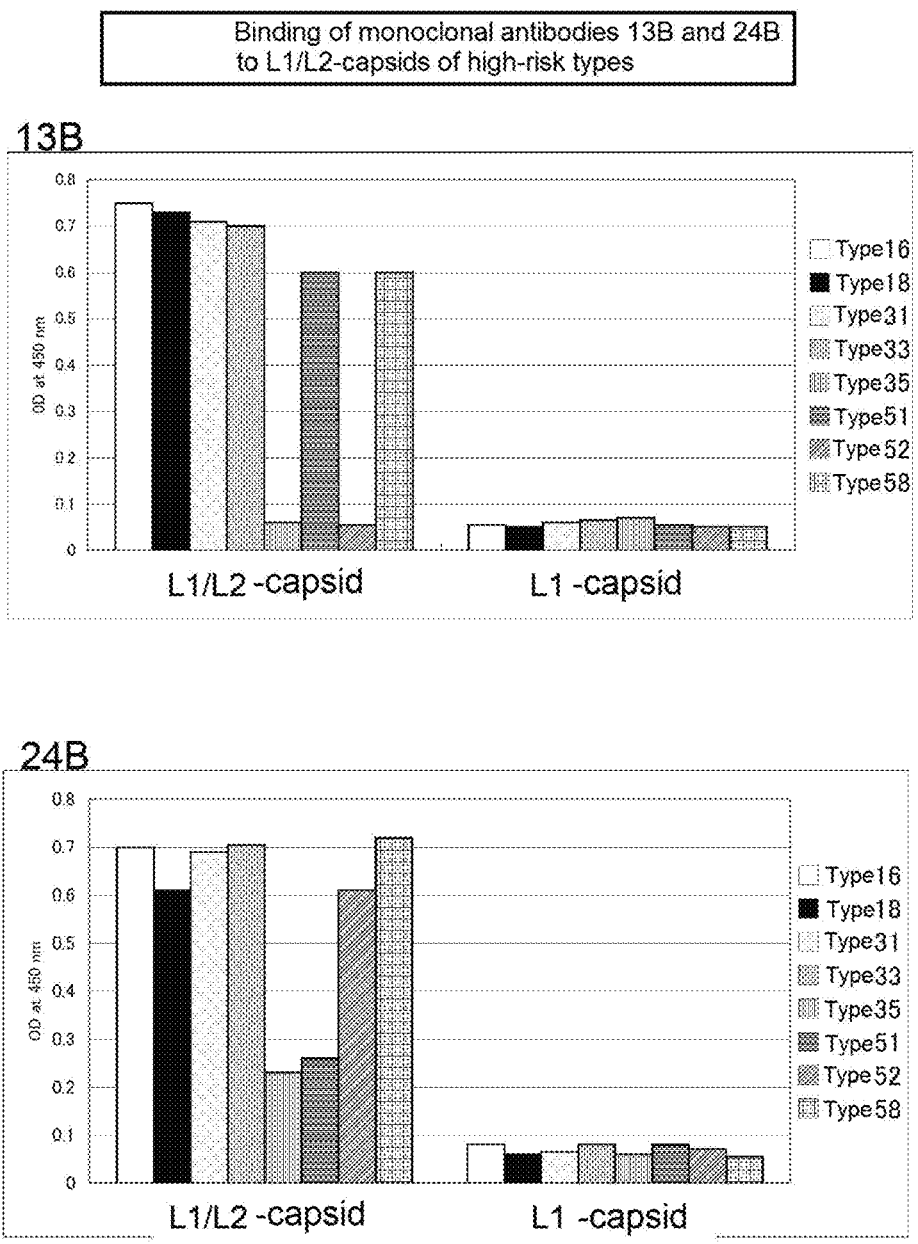
FIG. 11 shows binding of monoclonal antibodies 13B and 24B to L1/L2-capsids of high-risk types.

PsV diluted with phenol red-free cell culture medium and antibody-containing ascites (13B, 24B or a mixture thereof) were mixed and reacted at 4° C. for 1 hour, and then infected into 293FT cells which had been plated in 96-well plates. After 3 days, 40 µl of the culture supernatant was collected and mixed with 20 µl of a 0.05% CHAPS solution and 200 µl of a substrate solution (one tablet of 4-Nitrophenyl phosphate disodium salt hexahydrate (Sigma N9389) was added to 20 ml of a solution containing 9.5 M Diethanolamine, 1 mM $MgCl_2$ and 0.5 mM $ZnCl_2$). After color development, the absorbance at 450 nm was measured. The infectivity of PsV when mixed with each antibody was compared with the infectivity of PsV when mixed with mouse serum (preimmune, diluted 1:50) (negative control).
(Results)
13B and 24B were both found to have neutralizing activity against HPV16 and HPV58 pseudoviruses, and a mixture of antibodies 13B and 24B showed stronger neutralizing activity than antibody 13B or 24B alone (FIG. 3).
(2) Moreover, antibodies 13B and 24B were also analyzed for their neutralizing activity against HPV18, 31, 33, 35, 51 and 52 pseudoviruses, in addition to HPV16 and HPV58, in the same manner as shown in (1) above. In this analysis, anti-FLAG monoclonal antibody M2 (50 µg/ml) was used as a negative control, and monoclonal antibodies (50 µg/ml) purified from mouse ascites were used as antibodies 13B and 24B. An antibody solution (anti-FLAG antibody M2, 13B, 24B or a mixture of 13B and 24B) and a PsV suspension were mixed to give an antibody concentration of 25 µg/mL. Moreover, the infectivity of PsV when mixed with each antibody was compared with the infectivity of PsV when mixed with the negative control (anti-FLAG antibody M2), followed by t-test to determine the presence or absence of neutralizing activity for each antibody.
(Results)
13B was found to neutralize HPV16, 18, 31, 33, 51 and 58, while 24B was found to neutralize HPV16, 18, 31, 33, 35, 51, 52 and 58. Namely, 13B neutralized all types of pseudoviruses, except for HPV35 and HPV52, among the pseudoviruses tested. 24B neutralized all types of pseudoviruses tested. Moreover, a mixture of 13B and 24B showed stronger neutralizing activity than alone (FIG. 10).
(Test Method 2) Measurement of Binding Activity of Monoclonal Antibodies to L1/L2-Capsids of High-Risk Types
(1) L1 and L2 expression plasmids for each type of HPV were transfected into 293FT cells. Extraction and purification of L1/L2-capsid from the transfected cells was performed in the same manner as used for PsV (see Test Method 1).
To each well of 96-well ELISA plates, the L1/L2-capsid diluted with PBS (0.5 µg/ml) was added in a volume of 50 µl and allowed to stand overnight at 4° C. The plates were blocked with a blocking solution (PBS containing 5% skimmed milk and 0.1% Tween 20) at room temperature for 2 hours to prepare antigen-immobilized plates.
Ascites containing each monoclonal antibody was diluted 1:100 with the blocking solution and reacted with the L1/L2-capsid immobilized on the ELISA plates. After washing with PBST, horseradish peroxidase (HRP)-labeled anti-mouse IgG antibody (Santa Cruz: sc-2031) diluted 1:2000 with the blocking solution was added to each well and reacted at room temperature for 1 hour. After washing with PBST, a substrate solution (2 mg/ml o-phenylenediamine and 0.0065% aqueous hydrogen peroxide in 0.1 M trisodium citrate, pH 4.8) was added to each well and reacted at room temperature. After color development, the absorbance at 450 nm was measured.
(Results)
13B and 24B were bound to L1/L2-capsids of types 16, 31, 33, 51 and 58 and L1/L2-capsids of types 16, 31, 33, 35,
51, 52 and 58, respectively, as analyzed by ELISA. Namely, 13B was bound to all the antigens tested, except for types 35 and 52. 24B was bound to all the antigens tested.
21A (an antibody which was bound to a peptide having a sequence covering amino acids 56-75 of the HPV type 16 L2 protein during hybridoma selection in Example 1, but has no neutralizing activity against HPV16 pseudovirus) was bound to none of the antigens tested (FIG. 4).
(2) Moreover, 13B and 24B were also analyzed for their binding to type 18 L1/L2-capsid, in addition to the L1/L2-capsids of types 16, 31, 33, 35, 51, 52 and 58 tested above, in the same manner as shown in (1) above. Likewise, a capsid consisting only of L1 was prepared and each antibody was analyzed for its biding to this capsid in the same manner as shown in (1) above. Each monoclonal antibody purified from mouse ascites was diluted to 250 ng/well with the blocking solution before use.
(Results)
13B and 24B were also bound to the type 18 L1/L2-capsid. Namely, 13B was bound to all the antigens tested, except for types 35 and 52. 24B was bound to all the antigens tested. Moreover, none of the antibodies was bound to the capsid consisting only of L1, indicating that these antibodies were specifically bound to the L2 protein of each type (FIG. 11).
(Test Method 3) Measuring of Cross-Neutralizing Antibody Titers in Serum
HPV16 L1/L2-capsid for use as an antigen was prepared by infecting insect cells (Sf9) with HPV16 L1- and L2-expressing baculovirus. At 3 days after viral infection, the cells were suspended in PBS containing 0.5% NP-40 to separate their nuclei. The nuclei were suspended in PBS containing cesium chloride (1.28 g/ml) and homogenized by ultrasonication. The homogenate was centrifuged at 34,000 rpm at 20° C. for 20 hours to collect a fraction containing the L1/L2-capsid. The fraction was dialyzed overnight against PBS containing 0.5 M sodium chloride. In an ultracentrifugal tube, PBS solutions containing 5% and 60% sucrose were overlaid in this order from the top, onto which the dialyzed fraction was further overlaid, followed by centrifugation at 31,000 rpm at 4° C. for 2 hours. A fraction containing the L1/L2-capsid was dialyzed overnight against PBS containing 0.5 M sodium chloride and used as an antigen.
To each well of 96-well ELISA plates, the HPV16 L1/L2-capsid diluted with PBS (5 µg/ml) was added in a volume of 50 µl and allowed to stand overnight at 4° C. The plates were blocked with PBST (PBS containing 0.1% Tween-20) containing 5% skimmed milk at room temperature for 2 hours to prepare antigen-immobilized plates.
Serial dilutions of test sera, such as rabbit anti-P56/75 serum and control serum, prepared by being serially diluted with the blocking solution in 5-fold increments from 1/10 to 1/6250, were each added to the wells of the antigen-immobilized plates and reacted at room temperature for 2 hours. The test sera used were rabbit sera immunized with KLH-P53/69 (a peptide having the amino acid sequence of P53/69 [SEQ ID NO: 23] conjugated with KLH via cysteine), KLH-P56/75, KLH-P18/38 (WO2009/001867) or 16L1-430(56/75) chimeric capsid (WO2009/001867). The KLH used was "Imject® mcKLH (in PBS Buffer)" (Thermo Scientific Pierce). After washing with PBST, the plates were reacted at room temperature for 2 hours with 13B and 24B mouse ascites diluted 1:100000 and 1:3000, respectively, with the blocking solution. After washing with PBST, horseradish peroxidase (HRP)-labeled anti-mouse IgG antibody (Santa Cruz: sc-2031) diluted 1:2000 with the blocking solution was added to each well and reacted at room temperature for 1 hour. After washing with PBST, a substrate solution (2 mg/ml o-phenylenediamine and 0.0065% aqueous hydrogen peroxide in 0.1 M trisodium citrate, pH 4.8) was added and reacted at room temperature. After color development, the absorbance at 450 nm was measured. The absorbance data obtained for 1/50, 1/250 and 1/1250 dilutions of each test serum were used to quantify the cross-neutralizing antibody titer of each serum by parallel line assay.

(Results)

Figure 5:
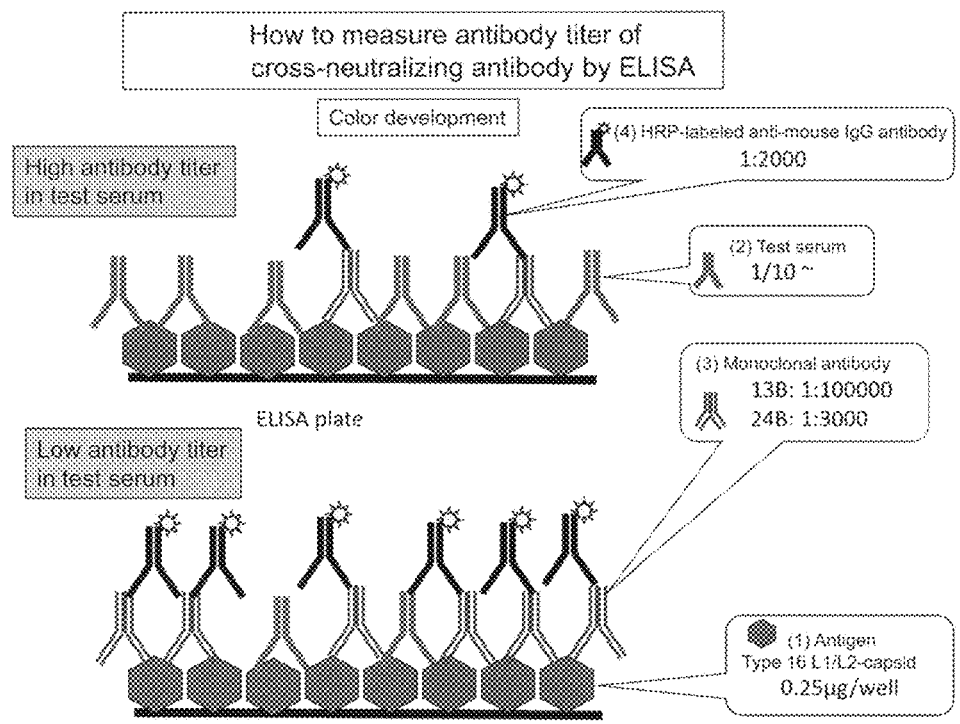
FIG. 5 shows how to measure cross-neutralizing antibody titers by ELISA using monoclonal antibodies 13B and 24B.

The rabbit sera immunized with KLH-P56/75 and 16L1-430(56/75) chimeric capsid were found to contain an antibody inhibiting the binding of monoclonal antibody 13B. The rabbit sera immunized with KLH-P53/69, KLH-P56/75 and 16L1-430(56/75) were found to contain an antibody inhibiting the binding of monoclonal antibody 24B. The rabbit serum immunized with KLH-P18/38 used as a negative control contained no antibody inhibiting the binding of these monoclonal antibodies (FIGS. 5 and 6).

Figure 6:
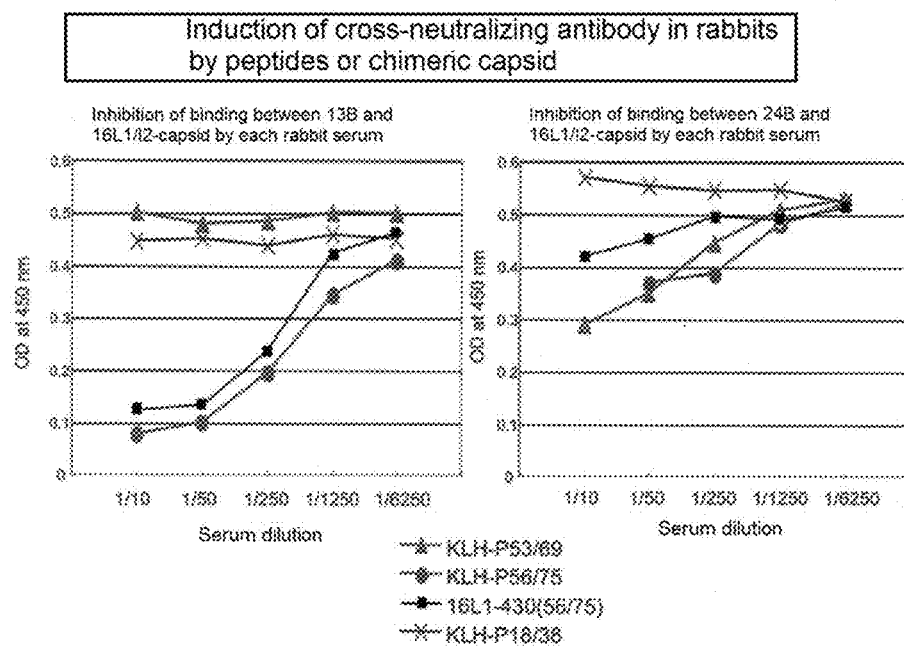
FIG. 6 shows cross-neutralizing antibody induced in rabbits immunized with KLH-conjugated peptides or a chimeric capsid.

Based on the results of ELISA in FIG. 6, antibody titers were quantified. The rabbit serum immunized with KLH-P56/75 was used as a standard serum, and the cross-neutralizing antibody titer of each rabbit serum was quantified from the OD values obtained for 1/50, 1/250 and 1/1250 dilutions by parallel line assay. The results obtained are shown in the table below.

ID NO: 5]. The light chains of 13B and 24B were each amplified by PCR with a primer for an adaptor and a primer for κ chain constant region (5'-GGATACAGTTGGTGCA-GCATC) [SEQ ID NO: 6]. After the PCR products were electrophoresed on an agarose gel, bands were excised and each cloned into a pGEM-T Easy vector (Promega). About 10 clones of each chain were analyzed for their nucleotide sequences to eliminate sequences probably resulting from PCR errors. Amino acid sequences were deduced from the nucleotide sequences of the cDNAs.

The affinity purified 13B and 24B were electrophoresed on a polyacrylamide gel and then transferred onto a PVDF membrane, and N-terminal amino acid sequences (5 residues) of their heavy and light chains were analyzed by the Edman degradation method, thereby confirming that they were matched with the amino acid sequences deduced from the nucleotide sequences.

The amino acid sequences of variable regions in 13B and 24B are shown in Table 2. Further, the sequences of their complementarity determining regions (CDRs) 1 to 3 are shown in Table 3.

Likewise, FIG. 7 shows the amino acid sequences of variable regions in 13B and 24B, along with their complementarity determining regions (CDRs) 1 to 3.

TABLE 1

Quantification of cross-neutralizing antibody titers by parallel line assay

Antibody titers of antibody inhibiting 13B binding

|  | Serum dilution | OD at 450 nm | | | PLL value (antibody titer) |
| --- | --- | --- | --- | --- | --- |
|  |  | 1/50 | 1/250 | 1/1250 |  |
| Standard serum → | KLH-P56/75 | 0.1 | 0.195 | 0.344 | 10.0000 |
|  | 16L1-430(56/75) | 0.133 | 0.237 | 0.425 | 5.3839 |
|  | KLH-P53/69 | 0.478 | 0.484 | 0.5 | 0.0846 |
|  | KLH-P18/38 | 0.45 | 0.437 | 0.458 | 0.1170 |

Antibody titers of antibody inhibiting 24B binding

|  | Serum dilution | OD at 450 nm | | | PLL value (antibody titer) |
| --- | --- | --- | --- | --- | --- |
|  |  | 1/50 | 1/250 | 1/1250 |  |
| Standard serum → | KLH-P56/75 | 0.369 | 0.387 | 0.481 | 10.0000 |
|  | 16L1-430(56/75) | 0.453 | 0.495 | 0.489 | 0.5293 |
|  | KLH-P53/69 | 0.349 | 0.444 | 0.507 | 6.3672 |
|  | KLH-P18/38 | 0.552 | 0.544 | 0.545 | 0.0062 |

4. Subtype Analysis of Monoclonal Antibodies 13B and 24B 13B and 24B were affinity purified using KLH-P56/75-immobilized sepharose 4B (GE Healthcare). The purified antibodies were analyzed for their subtypes using a Mouse Monoclonal Antibody Isotyping Test Kit (AbD Serotec). 13B was found to be IgG1, while 24B was found to be IgG2b. Their light chains were each a κ chain.

5. Analysis of Variable Region Amino Acid Sequences in Monoclonal Antibodies 13B and 24B From 13B- and 24B-producing hybridomas (accession Nos. FERM BP-11304 and FERM BP-11305), RNAs were extracted using an RNeasy Mini kit (QIAGEN). The RNAs were converted into cDNAs using a SMARTer RACE cDNA Amplification Kit (Clontech), simultaneously with adding an adaptor to the 5'-terminal end of each cDNA. The heavy chain of 13B was amplified by PCR with a primer for an adaptor and a primer for IgG1 constant region (5'-ATAGACAGATGGGGGTGTCGTTTTGGC) [SEQ ID NO: 4]. The heavy chain of 24B was amplified by PCR with a primer for an adaptor and a primer for IgG2b constant region (5'-AGGGGCCAGTGGATAGACTGATGG) [SEQ

TABLE 2

| Variable region in 13B | |
| --- | --- |
| Heavy chain | DVQLQESGPGLVKPSQSLSLSCTVTGYSITSDSAWNWIRQFPGN KLEWMGYITFSGSTNYNPSLKSRLSITRDTSKKQFFLQLNSVTT EDTATYYCTGPFLDYWGQGTTLTVSS (SEQ ID NO: 7) |
| Light Chain | DVVMTQTPLSLPVSLGDQATISCRSSLSLVLSNRITYLQWYLQK PGQSPKLLIYKVSNRFSGVPDRFSGSGSGTDFTLKISRVEAEDL GVYFCSQSSHRPWTFGGGTKLEIKRA (SEQ ID NO: 8) |

| Variable region in 24B | |
| --- | --- |
| Heavy chain | EVQLQQSGTVLARPGASVKMSCKASVYSFPSNWMHWVKQRPGQG LEWIGAIYPGTGATRYNQKFKDKAKLTAVTSADTAYMELSSLTD EDSAVYYCTGYSLYWGQGTILTVSS (SEQ ID NO: 9) |
| Light chain | DVVMTQTPLTLSVTLGQPASISCKSSQSLLDSDGKTYLNWLLQR PGQSPKRLIYLVSKLDSGVPDRFSGSGSGTDFTLRISRVEAEDL GVYYCWQGTHLPHAFGGGTTLEIKRA (SEQ ID NO: 10) |

TABLE 3

| Heavy chain | | SEQ ID NO: | Light chain | | SEQ ID NO: |
|---|---|---|---|---|---|
| CDR sequences of 13B | | | | | |
| CDRH1 | SDSAWN | 11 | CDRL1 | RSSLSLVLSNRITYLQ | 14 |
| CDRH2 | YITFSGSTNYNPSLKS | 12 | CDRL2 | KVSNRFS | 15 |
| CDRH3 | PFLDY | 13 | CDRL3 | SQSSHFPWT | 16 |
| CDR sequences of 24B | | | | | |
| CDRH1 | SNWMH | 17 | CDRL1 | KSSQSLLDSDGKTYLN | 20 |
| CDRH2 | AIYPGTGATRYNQKFKD | 18 | CDRL2 | LVSKLDS | 21 |
| CDRH3 | YSLY | 19 | CDRL3 | WQGTHLPHA | 22 |

INDUSTRIAL APPLICABILITY

The monoclonal antibody of the present invention has binding activity to high-risk types of HPV with a very large number of genotypes, and a method for antibody titer measurement using the monoclonal antibody of the present invention is a useful method which allows large-scale and rapid measurement of cross-neutralizing antibody titers in serum samples from subjects, e.g., in clinical studies aimed at the development of vaccines, particularly the practical use of next-generation HPV vaccines. Moreover, the monoclonal antibody of the present invention can also be used as a diagnostic or therapeutic agent for infection with high-risk types of HPV.

The invention claimed is:

1. A method for measuring the antibody titer of a cross-neutralizing antibody against human papillomavirus (HPV), which comprises the steps of:
 (a) bringing a test sample into contact with an HPV antigen to establish binding of cross-neutralizing antibodies in the sample to the antigen;
 (b) adding a monoclonal antibody comprising the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3) or a monoclonal antibody comprising the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3) to the reaction system in step (a);
 (c) contacting the monoclonal antibody bound to the antigen with a labeled secondary antibody recognizing the monoclonal antibody to determine the amount of the monoclonal antibody bound to the antigen; and
 (d) measuring signal intensity arising from the labeled secondary antibody bound to the monoclonal antibody in the presence and absence of the test sample, thereby determining the antibody titer of the cross-neutralizing antibody in the test sample.

2. A method for measuring the antibody titer of a cross-neutralizing antibody against human papillomavirus (HPV), which comprises the steps of:
 (a) bringing a test sample into contact with an HPV antigen to establish binding of cross-neutralizing antibodies in the sample to the antigen;
 (b) bringing residual epitopes, which remain unbound to the antibodies in step (a), into contact with a monoclonal antibody comprising the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3) or a monoclonal antibody comprising the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3);
 (c) contacting the monoclonal antibody bound to the residual epitopes with a labeled secondary antibody recognizing the monoclonal antibody to determine the amount of the monoclonal antibody bound to the epitopes; and (d) measuring signal intensity arising from the labeled secondary antibody bound to the monoclonal antibody in the presence and absence of the test sample, thereby determining the antibody titer of the cross-neutralizing antibody in the test sample.

3. A method for measuring the antibody titer of a cross-neutralizing antibody against human papillomavirus (HPV), which comprises the steps of:

(a) bringing a monoclonal antibody comprising the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3) or a monoclonal antibody comprising the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3) in admixture with a test sample into contact with an HPV antigen to form antibody/antigen conjugates;

(b) contacting the conjugates formed between the monoclonal antibody and the antigen in step (a) with a labeled secondary antibody recognizing the monoclonal antibody to determine the amount of the monoclonal antibody used to form antibody/antigen conjugates among those obtained in step (a); and (c) measuring signal intensity arising from the labeled secondary antibody bound to the monoclonal antibody in the presence and absence of the test sample or before and after addition of the test sample, thereby determining the antibody titer of the cross-neutralizing antibody in the test sample.

4. The method according to claim 1, wherein the HPV antigen is immobilized on a solid support.

5. A kit for determining the presence of cross-neutralizing antibody against HPV in a test sample, which comprises (a) an HPV antigen immobilized on a solid support, (b) a monoclonal antibody comprising the amino acid sequences shown in SEQ ID NO: 11 (CDRH1), SEQ ID NO: 12 (CDRH2), SEQ ID NO: 13 (CDRH3), SEQ ID NO: 14 (CDRL1), SEQ ID NO: 15 (CDRL2) and SEQ ID NO: 16 (CDRL3) or a monoclonal antibody comprising the amino acid sequences shown in SEQ ID NO: 17 (CDRH1), SEQ ID NO: 18 (CDRH2), SEQ ID NO: 19 (CDRH3), SEQ ID NO: 20 (CDRL1), SEQ ID NO: 21 (CDRL2) and SEQ ID NO: 22 (CDRL3), and (c) a labeled secondary antibody recognizing the monoclonal antibody.

6. The method according to claim 2, wherein the HPV antigen is immobilized on a solid support.

7. The method according to claim 3, wherein the HPV antigen is immobilized on a solid support.

* * * * *

SEQUENCE LISTING

```
<160> NUMBER OF SEQ ID NOS: 59

<210> SEQ ID NO 1
<211> LENGTH: 20
<212> TYPE: PRT
<213> ORGANISM: HPV 16

<400> SEQUENCE: 1

Gly Gly Leu Gly Ile Gly Thr Gly Ser Gly Thr Gly Gly Arg Thr Gly
1               5                   10                  15

Tyr Ile Pro Leu
            20

<210> SEQ ID NO 2
<211> LENGTH: 11
<212> TYPE: PRT
<213> ORGANISM: HPV 16

<400> SEQUENCE: 2

Gly Thr Gly Gly Arg Thr Gly Tyr Ile Pro Leu
1               5                   10

<210> SEQ ID NO 3
<211> LENGTH: 14
<212> TYPE: PRT
<213> ORGANISM: HPV 16

<400> SEQUENCE: 3

Gly Gly Leu Gly Ile Gly Thr Gly Ser Gly Thr Gly Gly Arg
1               5                   10

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
```

-continued atagacagat gggggtgtcg ttttggc                                             27

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
aggggccagt ggatagactg atgg                                                24

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ggatacagtt ggtgcagcat c                                                   21

<210> SEQ ID NO 7
<211> LENGTH: 114
<212> TYPE: PRT
<213> ORGANISM: Artificial Sequence
<220> FEATURE:
<223> OTHER INFORMATION: Hybrid Amino Acid Sequence

<400> SEQUENCE: 7

Asp Val Gln Leu Gln Glu Ser Gly Pro Gly Leu Val Lys Pro Ser Gln
1               5                   10                  15

Ser Leu Ser Leu Ser Cys Thr Val Thr Gly Tyr Ser Ile Thr Ser Asp
            20                  25                  30

Ser Ala Trp Asn Trp Ile Arg Gln Phe Pro Gly Asn Lys Leu Glu Trp
        35                  40                  45

Met Gly Tyr Ile Thr Phe Ser Gly Ser Thr Asn Tyr Asn Pro Ser Leu
    50                  55                  60

Lys Ser Arg Leu Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Gly Pro Phe Leu Asp Tyr Trp Gly Gln Gly Thr Thr Leu Thr Val
            100                 105                 110

Ser Ser

<210> SEQ ID NO 8
<211> LENGTH: 114
<212> TYPE: PRT
<213> ORGANISM: Artificial Sequence
<220> FEATURE:
<223> OTHER INFORMATION: Hybrid Amino Acid Sequence

<400> SEQUENCE: 8

Asp Val Val Met Thr Gln Thr Pro Leu Ser Leu Pro Val Ser Leu Gly
1               5                   10                  15

Asp Gln Ala Thr Ile Ser Cys Arg Ser Ser Leu Ser Leu Val Leu Ser
            20                  25                  30

Asn Arg Ile Thr Tyr Leu Gln Trp Tyr Leu Gln Lys Pro Gly Gln Ser
        35                  40                  45

-continued

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Ser His Phe Pro Trp Thr Phe Gly Gly Gly Thr Lys Leu Glu Ile Lys
            100                 105                 110

Arg Ala

<210> SEQ ID NO 9
<211> LENGTH: 113
<212> TYPE: PRT
<213> ORGANISM: Artificial Sequence
<220> FEATURE:
<223> OTHER INFORMATION: Hybrid Amino Acid Sequence

<400> SEQUENCE: 9

Glu Val Gln Leu Gln Gln Ser Gly Thr Val Leu Ala Arg Pro Gly Ala
1               5                   10                  15

Ser Val Lys Met Ser Cys Lys Ala Ser Val Tyr Ser Phe Pro Ser Asn
                20                  25                  30

Trp Met His Trp Val Lys Gln Arg Pro Gly Gln Gly Leu Glu Trp Ile
            35                  40                  45

Gly Ala Ile Tyr Pro Gly Thr Gly Ala Thr Arg Tyr Asn Gln Lys Phe
    50                  55                  60

Lys Asp Lys Ala Lys Leu Thr Ala Val Thr Ser Ala Asp Thr Ala Tyr
65                  70                  75                  80

Met Glu Leu Ser Ser Leu Thr Asp Glu Asp Ser Ala Val Tyr Tyr Cys
                85                  90                  95

Thr Gly Tyr Ser Leu Tyr Trp Gly Gln Gly Thr Ile Leu Thr Val Ser
            100                 105                 110

Ser

<210> SEQ ID NO 10
<211> LENGTH: 114
<212> TYPE: PRT
<213> ORGANISM: Artificial Sequence
<220> FEATURE:
<223> OTHER INFORMATION: Hybrid Amino Acid Sequence

<400> SEQUENCE: 10

Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Gly
                85                  90                  95

Thr His Leu Pro His Ala Phe Gly Gly Gly Thr Thr Leu Glu Ile Lys
            100                 105                 110

Arg Ala

```
<210> SEQ ID NO 11
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: MAb 13B VH CDR1

<400> SEQUENCE: 11

Ser Asp Ser Ala Trp Asn
1               5

<210> SEQ ID NO 12
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MAb 13B VH CDR2

<400> SEQUENCE: 12

Tyr Ile Thr Phe Ser Gly Ser Thr Asn Tyr Asn Pro Ser Leu Lys Ser
1               5                   10                  15

<210> SEQ ID NO 13
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MAb 13B VH CDR3

<400> SEQUENCE: 13

Pro Phe Leu Asp Tyr
1               5

<210> SEQ ID NO 14
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MAb 13B VL CDR1

<400> SEQUENCE: 14

Arg Ser Ser Leu Ser Leu Val Leu Ser Asn Arg Ile Thr Tyr Leu Gln
1               5                   10                  15

<210> SEQ ID NO 15
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: MAb 13B VL CDR2

<400> SEQUENCE: 15

Lys Val Ser Asn Arg Phe Ser
1               5

<210> SEQ ID NO 16
<211> LENGTH: 9
```

```
<212> TYPE: PRT
<213> ORGANISM: Mus musculus
<220> FEATURE:
<221> NAME/KEY: DOMAIN
<222> LOCATION: (1)..(9)
<223> OTHER INFORMATION: MAb 13B VL CDR3

<400> SEQUENCE: 16

Ser Gln Ser Ser His Phe Pro Trp Thr
1               5

<210> SEQ ID NO 17
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: MAb 24B VH CDR1

<400> SEQUENCE: 17

Ser Asn Trp Met His
1               5

<210> SEQ ID NO 18
<211> LENGTH: 17
<212> TYPE: PRT
<213> ORGANISM: Mus musculus
<220> FEATURE:
<221> NAME/KEY: DOMAIN
<222> LOCATION: (1)..(17)
<223> OTHER INFORMATION: MAb 24B VH CDR2

<400> SEQUENCE: 18

Ala Ile Tyr Pro Gly Thr Gly Ala Thr Arg Tyr Asn Gln Lys Phe Lys
1               5                   10                  15

Asp

<210> SEQ ID NO 19
<211> LENGTH: 4
<212> TYPE: PRT
<213> ORGANISM: Mus musculus
<220> FEATURE:
<221> NAME/KEY: DOMAIN
<222> LOCATION: (1)..(4)
<223> OTHER INFORMATION: MAb 24B VH CDR3

<400> SEQUENCE: 19

Tyr Ser Leu Tyr
1

<210> SEQ ID NO 20
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: MAb 24B VL CDR1

<400> SEQUENCE: 20

Lys Ser Ser Gln Ser Leu Leu Asp Ser Asp Gly Lys Thr Tyr Leu Asn
1               5                   10                  15

<210> SEQ ID NO 21
<211> LENGTH: 7
<212> TYPE: PRT
<213> ORGANISM: Mus musculus
```

```
<220> FEATURE:
<221> NAME/KEY: DOMAIN
<222> LOCATION: (1)..(7)
<223> OTHER INFORMATION: MAb 24B VL CDR2

<400> SEQUENCE: 21

Leu Val Ser Lys Leu Asp Ser
1               5

<210> SEQ ID NO 22
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: MAb 24B VL CDR3

<400> SEQUENCE: 22

Trp Gln Gly Thr His Leu Pro His Ala
1               5

<210> SEQ ID NO 23
<211> LENGTH: 17
<212> TYPE: PRT
<213> ORGANISM: HPV 16

<400> SEQUENCE: 23

Val Phe Phe Gly Gly Leu Gly Ile Gly Thr Gly Ser Gly Thr Gly Gly
1               5                   10                  15

Arg

<210> SEQ ID NO 24
<211> LENGTH: 10
<212> TYPE: PRT
<213> ORGANISM: HPV 16

<400> SEQUENCE: 24

Ser Gly Thr Gly Gly Arg Thr Gly Tyr Ile
1               5                   10

<210> SEQ ID NO 25
<211> LENGTH: 10
<212> TYPE: PRT
<213> ORGANISM: HPV 16

<400> SEQUENCE: 25

Leu Gly Ile Gly Thr Gly Ser Gly Thr Gly
1               5                   10

<210> SEQ ID NO 26
<211> LENGTH: 14
<212> TYPE: PRT
<213> ORGANISM: HPV 16

<400> SEQUENCE: 26

Ser Ala Thr Gln Leu Tyr Lys Thr Cys Lys Gln Ala Gly Thr
1               5                   10

<210> SEQ ID NO 27
<211> LENGTH: 21
<212> TYPE: PRT
<213> ORGANISM: HPV 16

<400> SEQUENCE: 27
```

Val Phe Phe Gly Gly Leu Gly Ile Gly Thr Gly Ser Gly Thr Gly Gly
1               5                   10                  15

Arg Thr Gly Tyr Ile
            20

<210> SEQ ID NO 28
<211> LENGTH: 21
<212> TYPE: PRT
<213> ORGANISM: HPV 16

<400> SEQUENCE: 28

Val Phe Phe Gly Gly Leu Gly Ile Gly Thr Gly Ser Gly Thr Gly Gly
1               5                   10                  15

Arg Thr Ala Ala Ala
            20

<210> SEQ ID NO 29
<211> LENGTH: 21
<212> TYPE: PRT
<213> ORGANISM: HPV 16

<400> SEQUENCE: 29

Val Phe Phe Gly Gly Leu Gly Ile Gly Thr Gly Ser Gly Thr Gly Ala
1               5                   10                  15

Ala Ala Ala Ala Ala
            20

<210> SEQ ID NO 30
<211> LENGTH: 21
<212> TYPE: PRT
<213> ORGANISM: HPV 16

<400> SEQUENCE: 30

Val Phe Phe Gly Gly Leu Gly Ile Gly Thr Gly Ser Ala Ala Ala Ala
1               5                   10                  15

Ala Ala Ala Ala Ala
            20

<210> SEQ ID NO 31
<211> LENGTH: 21
<212> TYPE: PRT
<213> ORGANISM: HPV 16

<400> SEQUENCE: 31

Ala Ala Ala Leu Gly Ile Gly Thr Gly Ser Gly Thr Gly Gly Arg Thr
1               5                   10                  15

Gly Tyr Ile Pro Leu
            20

<210> SEQ ID NO 32
<211> LENGTH: 21
<212> TYPE: PRT
<213> ORGANISM: HPV 16

<400> SEQUENCE: 32

Ala Ala Ala Ala Ala Ala Gly Thr Gly Ser Gly Thr Gly Gly Arg Thr
1               5                   10                  15

Gly Tyr Ile Pro Leu
            20

<210> SEQ ID NO 33
<211> LENGTH: 21

```
<212> TYPE: PRT
<213> ORGANISM: HPV 16

<400> SEQUENCE: 33

Ala Ala Ala Ala Ala Ala Ala Ala Ser Gly Thr Gly Arg Thr
1               5                   10                  15

Gly Tyr Ile Pro Leu
            20

<210> SEQ ID NO 34
<211> LENGTH: 26
<212> TYPE: PRT
<213> ORGANISM: HPV 16

<400> SEQUENCE: 34

Ser Met Gly Val Phe Phe Gly Gly Leu Gly Ile Gly Thr Gly Ser Gly
1               5                   10                  15

Thr Gly Gly Arg Thr Gly Tyr Ile Pro Leu
            20                  25

<210> SEQ ID NO 35
<211> LENGTH: 26
<212> TYPE: PRT
<213> ORGANISM: HPV 18

<400> SEQUENCE: 35

Ser Leu Gly Ile Phe Leu Gly Gly Leu Gly Ile Gly Thr Gly Ser Gly
1               5                   10                  15

Thr Gly Gly Arg Thr Gly Tyr Ile Pro Leu
            20                  25

<210> SEQ ID NO 36
<211> LENGTH: 26
<212> TYPE: PRT
<213> ORGANISM: HPV 31

<400> SEQUENCE: 36

Ser Met Gly Val Phe Phe Gly Gly Leu Gly Ile Gly Ser Gly Ser Gly
1               5                   10                  15

Thr Gly Gly Arg Thr Gly Tyr Val Pro Leu
            20                  25

<210> SEQ ID NO 37
<211> LENGTH: 26
<212> TYPE: PRT
<213> ORGANISM: HPV 33

<400> SEQUENCE: 37

Ser Leu Gly Val Phe Phe Gly Gly Leu Gly Ile Gly Thr Gly Ser Gly
1               5                   10                  15

Ser Gly Gly Arg Thr Gly Tyr Val Pro Ile
            20                  25

<210> SEQ ID NO 38
<211> LENGTH: 26
<212> TYPE: PRT
<213> ORGANISM: HPV 35

<400> SEQUENCE: 38

Ser Met Ala Val Phe Phe Gly Gly Leu Gly Ile Gly Ser Gly Ser Gly
1               5                   10                  15

Thr Gly Gly Arg Ser Gly Tyr Val Pro Leu
```

```
            20                  25

<210> SEQ ID NO 39
<211> LENGTH: 26
<212> TYPE: PRT
<213> ORGANISM: HPV 39

<400> SEQUENCE: 39

Ser Met Gly Val Phe Phe Gly Gly Leu Gly Ile Gly Thr Gly Ser Gly
1               5                   10                  15

Thr Gly Gly Arg Thr Gly Tyr Ile Pro Leu
            20                  25

<210> SEQ ID NO 40
<211> LENGTH: 26
<212> TYPE: PRT
<213> ORGANISM: HPV 45

<400> SEQUENCE: 40

Ser Leu Gly Ile Phe Leu Gly Gly Leu Gly Ile Gly Thr Gly Thr Gly
1               5                   10                  15

Ser Gly Gly Arg Thr Gly Tyr Val Pro Leu
            20                  25

<210> SEQ ID NO 41
<211> LENGTH: 26
<212> TYPE: PRT
<213> ORGANISM: HPV 51

<400> SEQUENCE: 41

Gly Leu Gly Ile Phe Leu Gly Gly Leu Gly Ile Gly Thr Gly Ser Gly
1               5                   10                  15

Ser Gly Gly Arg Thr Gly Tyr Ile Pro Leu
            20                  25

<210> SEQ ID NO 42
<211> LENGTH: 26
<212> TYPE: PRT
<213> ORGANISM: HPV 52

<400> SEQUENCE: 42

Ser Leu Gly Val Phe Phe Gly Gly Leu Gly Ile Gly Thr Gly Ala Gly
1               5                   10                  15

Ser Gly Gly Arg Ala Gly Tyr Val Pro Leu
            20                  25

<210> SEQ ID NO 43
<211> LENGTH: 26
<212> TYPE: PRT
<213> ORGANISM: HPV 56

<400> SEQUENCE: 43

Ser Leu Phe Thr Tyr Phe Gly Gly Leu Gly Ile Gly Thr Gly Thr Gly
1               5                   10                  15

Ser Gly Gly Arg Ala Gly Tyr Val Pro Leu
            20                  25

<210> SEQ ID NO 44
<211> LENGTH: 26
<212> TYPE: PRT
<213> ORGANISM: HPV 58

<400> SEQUENCE: 44
```

-continued

Ser Leu Gly Val Phe Phe Gly Gly Leu Gly Ile Gly Thr Gly Ser Gly
1               5                   10                  15

Thr Gly Gly Arg Thr Gly Tyr Val Pro Leu
            20                  25

<210> SEQ ID NO 45
<211> LENGTH: 26
<212> TYPE: PRT
<213> ORGANISM: HPV 59

<400> SEQUENCE: 45

Ser Leu Gly Ile Phe Leu Gly Gly Leu Gly Ile Gly Thr Gly Ser Gly
1               5                   10                  15

Thr Gly Gly Arg Thr Gly Tyr Ile Pro Leu
            20                  25

<210> SEQ ID NO 46
<211> LENGTH: 26
<212> TYPE: PRT
<213> ORGANISM: HPV 66

<400> SEQUENCE: 46

Ser Leu Phe Thr Tyr Phe Gly Gly Leu Gly Ile Gly Thr Gly Ser Gly
1               5                   10                  15

Ser Gly Gly Arg Ala Gly Tyr Val Pro Leu
            20                  25

<210> SEQ ID NO 47
<211> LENGTH: 26
<212> TYPE: PRT
<213> ORGANISM: HPV 68

<400> SEQUENCE: 47

Ser Leu Gly Ile Phe Leu Gly Gly Leu Gly Ile Gly Thr Gly Ser Gly
1               5                   10                  15

Thr Gly Gly Arg Thr Gly Tyr Ile Pro Leu
            20                  25

<210> SEQ ID NO 48
<211> LENGTH: 26
<212> TYPE: PRT
<213> ORGANISM: HPV 73

<400> SEQUENCE: 48

Ser Ile Gly Val Phe Phe Gly Gly Leu Gly Ile Gly Ser Gly Ser Gly
1               5                   10                  15

Ser Gly Gly Arg Thr Gly Tyr Val Pro Leu
            20                  25

<210> SEQ ID NO 49
<211> LENGTH: 26
<212> TYPE: PRT
<213> ORGANISM: HPV 6

<400> SEQUENCE: 49

Ser Leu Gly Val Phe Phe Gly Gly Leu Gly Ile Gly Thr Gly Ser Gly
1               5                   10                  15

Thr Gly Gly Arg Thr Gly Tyr Val Pro Leu
            20                  25

<210> SEQ ID NO 50

```
<211> LENGTH: 26
<212> TYPE: PRT
<213> ORGANISM: HPV 11

<400> SEQUENCE: 50

Ser Leu Gly Val Phe Phe Gly Gly Leu Gly Ile Gly Thr Gly Ala Gly
1               5                   10                  15

Ser Gly Gly Arg Ala Gly Tyr Ile Pro Leu
            20                  25

<210> SEQ ID NO 51
<211> LENGTH: 26
<212> TYPE: PRT
<213> ORGANISM: HPV 2

<400> SEQUENCE: 51

Ser Leu Gly Val Phe Phe Gly Gly Leu Gly Ile Gly Thr Gly Ser Gly
1               5                   10                  15

Thr Gly Gly Arg Thr Gly Tyr Ile Pro Val
            20                  25

<210> SEQ ID NO 52
<211> LENGTH: 26
<212> TYPE: PRT
<213> ORGANISM: HPV 27

<400> SEQUENCE: 52

Ser Leu Gly Val Phe Phe Gly Gly Leu Gly Ile Gly Thr Gly Ser Gly
1               5                   10                  15

Thr Gly Gly Arg Thr Gly Tyr Ile Pro Val
            20                  25

<210> SEQ ID NO 53
<211> LENGTH: 14
<212> TYPE: PRT
<213> ORGANISM: HPV 16

<400> SEQUENCE: 53

Pro Pro Asp Ile Ile Pro Lys Val Glu Gly Lys Thr Ile Ala
1               5                   10

<210> SEQ ID NO 54
<211> LENGTH: 17
<212> TYPE: PRT
<213> ORGANISM: HPV 16

<400> SEQUENCE: 54

Gly Ile Gly Thr Gly Ser Gly Thr Gly Gly Arg Thr Gly Tyr Ile Pro
1               5                   10                  15

Leu

<210> SEQ ID NO 55
<211> LENGTH: 17
<212> TYPE: PRT
<213> ORGANISM: HPV 16

<400> SEQUENCE: 55

Ala Ala Ala Thr Gly Ser Gly Thr Gly Gly Arg Thr Gly Tyr Ile Pro
1               5                   10                  15

Leu

<210> SEQ ID NO 56
```

```
<210> SEQ ID NO 56
<211> LENGTH: 17
<212> TYPE: PRT
<213> ORGANISM: HPV 16

<400> SEQUENCE: 56

Ala Ala Ala Ala Ala Ala Gly Thr Gly Gly Arg Thr Gly Tyr Ile Pro
1               5                   10                  15

Leu

<210> SEQ ID NO 57
<211> LENGTH: 17
<212> TYPE: PRT
<213> ORGANISM: HPV 16

<400> SEQUENCE: 57

Gly Gly Leu Gly Ile Gly Thr Gly Ser Gly Thr Gly Gly Arg Thr Gly
1               5                   10                  15

Tyr

<210> SEQ ID NO 58
<211> LENGTH: 17
<212> TYPE: PRT
<213> ORGANISM: HPV 16

<400> SEQUENCE: 58

Gly Gly Leu Gly Ile Gly Thr Gly Ser Gly Thr Gly Gly Arg Ala Ala
1               5                   10                  15

Ala

<210> SEQ ID NO 59
<211> LENGTH: 17
<212> TYPE: PRT
<213> ORGANISM: HPV 16

<400> SEQUENCE: 59

Gly Gly Leu Gly Ile Gly Thr Gly Ser Gly Thr Ala Ala Ala Ala Ala
1               5                   10                  15

Ala
```